(12) United States Patent
Ramadass et al.

(10) Patent No.: US 10,844,423 B2
(45) Date of Patent: Nov. 24, 2020

(54) METHODS OF DETECTING LONG RANGE CHROMOSOMAL INTERACTIONS

(71) Applicant: Oxford Biodynamics PLC, Oxford (GB)

(72) Inventors: Aroul Selvam Ramadass, Yarnton (GB); Alexandre Akoulitchev, Yarnton (GB); Elizabeth Jane Mellor, Yarnton (GB)

(73) Assignee: OXFORD BIODYNAMICS PLC, Oxford (GB)

(*) Notice: Subject to any disclaimer, the term of this patent is extended or adjusted under 35 U.S.C. 154(b) by 182 days.

(21) Appl. No.: 13/922,790

(22) Filed: Jun. 20, 2013

(65) Prior Publication Data

US 2014/0162271 A1 Jun. 12, 2014

Related U.S. Application Data

(63) Continuation of application No. 12/995,261, filed as application No. PCT/GB2009/001377 on Jun. 2, 2009, now abandoned.

(30) Foreign Application Priority Data

Jun. 2, 2008 (GB) .................................. 0810051.3

(51) Int. Cl.
  *C12Q 1/6806* (2018.01)
  *A61P 43/00* (2006.01)
(52) U.S. Cl.
  CPC .................................. *C12Q 1/6806* (2013.01)
(58) Field of Classification Search
  CPC .... C12Q 1/6806; A61P 43/00; A61K 31/7088
  See application file for complete search history.

(56) References Cited

FOREIGN PATENT DOCUMENTS

WO WO 2007/057785 A2 5/2007
WO WO 2007093819 A2 * 8/2007

OTHER PUBLICATIONS

Palstra et al (2003) "The beta-globin nuclear compartment in development and erythroid differentiation." Nature Genetics 35(2):190-194.*

(Continued)

*Primary Examiner* — Jeremy C Flinders
(74) *Attorney, Agent, or Firm* — McKee, Voorhees & Sease, PLC

(57) ABSTRACT

The present invention relates to a method of monitoring epigenetic changes comprising monitoring changes in conditional long range chromosomal interactions at at least one chromosomal locus where the spectrum of long range interaction is associated with a specific physiological condition, the method comprising the steps of:—

Figure 1:
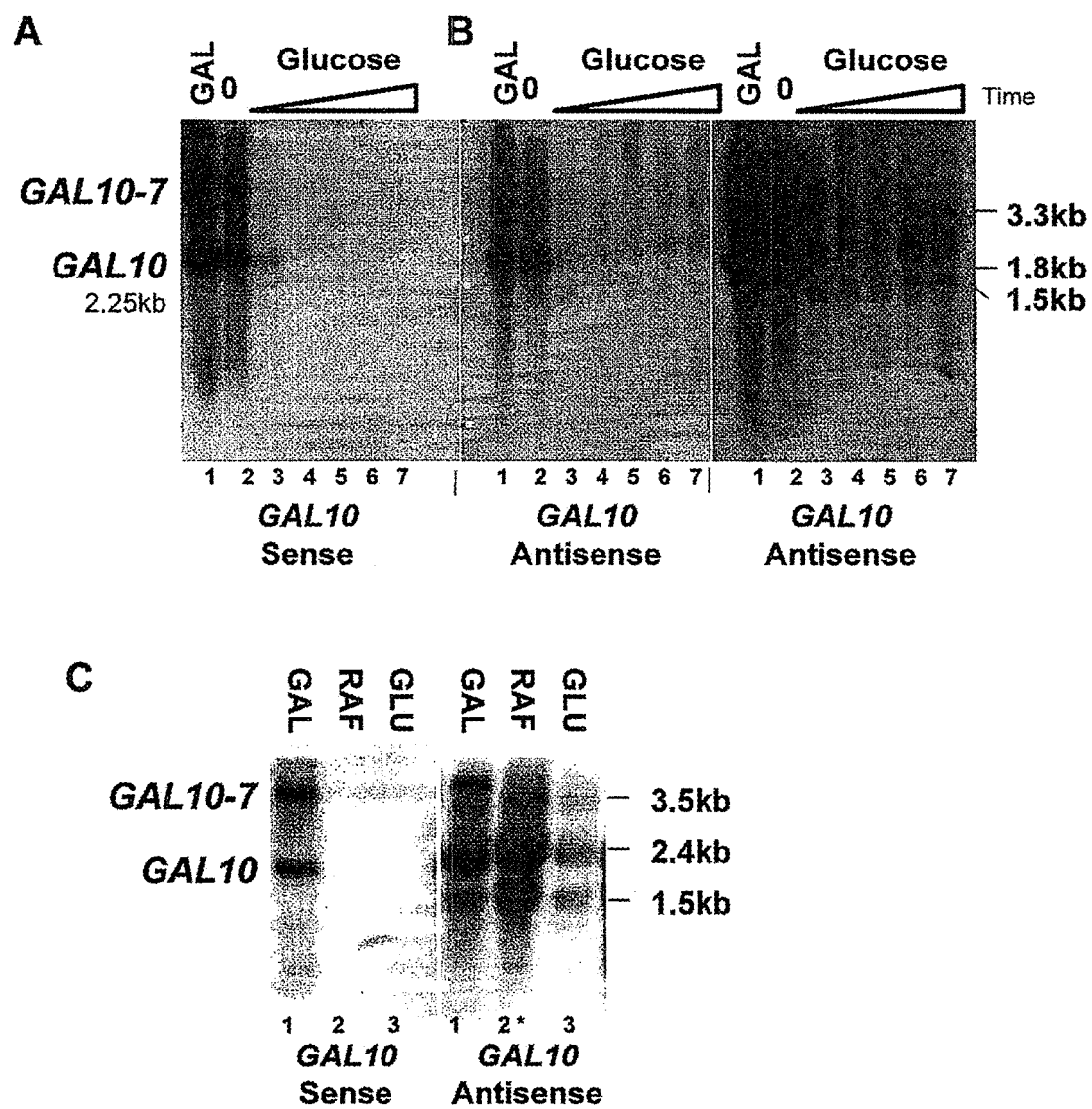

(i) in vitro crosslinking of said long range chromosomal interactions present at the at least one chromosomal locus;
(ii) isolating the cross linked DNA from said chromosomal locus;
(iii) subjecting said cross linked DNA to restriction digestion with an enzyme that cuts at least once within the at least one chromosomal locus;
(iv) ligating said cross linked cleaved DNA ends to form DNA loops;
(v) identifying the presence of said DNA loops;
wherein the presence of DNA loops indicates the presence of a specific long range chromosomal interaction.

1 Claim, 11 Drawing Sheets

Specification includes a Sequence Listing.

(56) References Cited

OTHER PUBLICATIONS

Kurukuti et al. (2006) "CTCF binding at the H19 imprinting control region mediates maternally inherited higher-order chromatin conformation to restrict enhancer access to Igf2" Proc. Natl. Acad. Sci. USA 103(28):10684-10689.*

Splinter et al. (2004) "3C technology: analyzing the spatial organization of genomic loci in vivo." Methods in Enzymology 375:493-507.*

Würtele et al. (2006) "Genome-wide scanning of HoxB1-associated loci in mouse ES cells using an open-ended Chromosome Conformation Capture methodology" Chromosome Research 14(5):477-495.*

Simonis et al. (2007) "An evaluation of 3C-based methods to capture DNA interactions" Nature Methods 4(11):895-901.*

Ansari, Athar et al., "A role for the CPF 3'-end processing machinery in RNAP II-dependent gene looping", Downloaded from genesdev.cshlp.org on Sep. 13, 2011, Genes & Development 19: 2969-2978, 2005.

Babu, M Madan et al., "Eukaryotic gene regulation in three dimensions and its impact on genome evolution" ScienceDirect, Current Opinion in Genetics & Development, 2008, 18:571-582.

Bickmore, Wendy A. et al., "Perturbations of chromatin structure in human genetic disease: recent advances", Human Molecular Genetics, 2003, vol. 12, Review Issue 2, R207-R213.

Brown, Carolyn J. et al., "Beyond sense: the role of antisense RNA in controlling Xist expression", Seminars in Cell & Developmental Biology 14 (2003), 341-347.

Dekker, Job, "A closer look at long-range chromosomal interactions", TRENDS in Biochemical Sciences, vol. 28, No. 6, Jun. 2003, 277-280.

Horike, Shin-ichi et al., "Loss of silent-chromatin looping and impaired imprinting of DLX5 in Rett syndrome", Nature Genetics, vol. 37, No. 1, Jan. 2005, pp. 31-40.

Kadauke, Stephan et al., "Chromatin loops in gene regulation", Biochim Biophys Acta. Jan. 2009; 1789(1):17-25.

Mattick, John S. et al., "Non-coding RNA", Human Molecular Genetics, 2006, vol. 15, Review Issue 1, pp. R17-R29.

O'Sullivan, Justin M. et al., "Gene loops juxtapose promoters and terminators in yeast", Nature Genetics, vol. 36, No. 9, Sep. 2004, pp. 1014-1018.

Pauler, Florian M. et al., "Silencing by imprinted noncoding RNAs: is transcription the answer?" Trends Genet. Jun. 2007; 23(6) 284-292.

Tolhuis, Bas et al., "Looping and interaction between hypersensitive sites in the active β-globin locus", Molecular Cell, 2002, vol. 10, No. 6, 1454-1465.

Tufarelli, Cristina et al., "Transcription of antisense RNA leading to gene silencing and methylation as a novel cause of human genetic disease", Nature Genetics, vol. 34, No. 2, Jun. 2003, pp. 157-165.

Oxford Biodynamics Limited, PCT/GB2009/001377, International Search Report dated Aug. 3, 2009.

Kleinjan, Dirk A. et al., "Long-Range Gene control and Genetic Disease", Advances in Genetics, vol. 61, pp. 340-388, 2008.

Kleinjan, Dirk A. et al., "Long-Range Control of Gene Expression: Emerging Mechanisms and Disruption in Disease", Am. J. Hum. Genet, 2005, 76:8-32.

McBride, David et al., "Rounding up active cis-elements in the triple C corral: Combining conservation, cleavage and conformation capture for the analysis of regulatory gene domains", Briefings in Functional Genomics and Proteomics, vol. 3, No. 3, pp. 267-279, Nov. 2004.

Oxford Biodynamics Limited, PCT/GB2009/001377, Examination Report from the United Kingdom Intellectual Property Office dated Nov. 2, 2012.

Zhao et al., "Circular chromosome conformation capture (4C) uncovers extensive networks of epigenetically regulated intra- and interchromosomal interactions", Oct. 8, 2006, Nature Genetics, vol. 38, 11: 1341-1347.

F.J. Dye, "Dictionary of Developmental Biology and Embryology", Wiley (2002), online version, one page.

Dekker, Job, "The three 'C's of chromosome conformation capture: controls, controls, controls", Nature Methods, vol. 3, No. 1, Jan. 2006, pp. 17-21.

Horike, Nucleic Acid and Enzyme, 2005, vol. 50, No. 8, pp. 978-984 (Japanese).

Horike, Nucleic Acid and Enzyme, 2005, vol. 50, No. 8, pp. 978-984, English Translation.

* cited by examiner

A

B

C

GAL10 antisense
Glucose

3C

ChIP Pol II

ChIP CTCF

SEQUENCE LISTING

<160> NUMBER OF SEQ ID NOS: 73

<210> SEQ ID NO 1
<211> LENGTH: 15
<212> TYPE: DNA
<213> ORGANISM: Artificial Sequence
<220> FEATURE:
<223> OTHER INFORMATION: Primer

<400> SEQUENCE: 1
ctgtaaaaga gttgc                                                      15

<210> SEQ ID NO 2
<211> LENGTH: 14
<212> TYPE: DNA
<213> ORGANISM: Artificial Sequence
<220> FEATURE:
<223> OTHER INFORMATION: Primer

<400> SEQUENCE: 2
ctgcaacatc caat                                                       14

<210> SEQ ID NO 3
<211> LENGTH: 15
<212> TYPE: DNA
<213> ORGANISM: Artificial Sequence
<220> FEATURE:
<223> OTHER INFORMATION: Primer

<400> SEQUENCE: 3
aaggaccact cttac                                                      15

<210> SEQ ID NO 4
<211> LENGTH: 14
<212> TYPE: DNA
<213> ORGANISM: Artificial Sequence
<220> FEATURE:
<223> OTHER INFORMATION: Primer

<400> SEQUENCE: 4
catgtgaaac caac                                                       14

<210> SEQ ID NO 5
<211> LENGTH: 15
<212> TYPE: DNA

```
<213> ORGANISM: Artificial Sequence
<220> FEATURE:
<223> OTHER INFORMATION: Primer

<400> SEQUENCE: 5
ctactttacc aaacg                                                    15

<210> SEQ ID NO 6
<211> LENGTH: 15
<212> TYPE: DNA
<213> ORGANISM: Artificial Sequence
<220> FEATURE:
<223> OTHER INFORMATION: Primer

<400> SEQUENCE: 6
caaggttaca caatc                                                    15

<210> SEQ ID NO 7
<211> LENGTH: 14
<212> TYPE: DNA
<213> ORGANISM: Artificial Sequence
<220> FEATURE:
<223> OTHER INFORMATION: Primer

<400> SEQUENCE: 7
cttcaccagc agtc                                                     14

<210> SEQ ID NO 8
<211> LENGTH: 14
<212> TYPE: DNA
<213> ORGANISM: Artificial Sequence
<220> FEATURE:
<223> OTHER INFORMATION: Primer

<400> SEQUENCE: 8
gcaagatagc aaac                                                     14

<210> SEQ ID NO 9
<211> LENGTH: 15
<212> TYPE: DNA
<213> ORGANISM: Artificial Sequence
<220> FEATURE:
<223> OTHER INFORMATION: Primer

<400> SEQUENCE: 9
ttagctctac cacag                                                    15

<210> SEQ ID NO 10
<211> LENGTH: 14
<212> TYPE: DNA
<213> ORGANISM: Artificial Sequence
<220> FEATURE:
<223> OTHER INFORMATION: Primer

<400> SEQUENCE: 10
tggttatgaa gagg                                                     14

<210> SEQ ID NO 11
<211> LENGTH: 14
<212> TYPE: DNA
<213> ORGANISM: Artificial Sequence
<220> FEATURE:
<223> OTHER INFORMATION: Primer

<400> SEQUENCE: 11
caaggctcat tgtc                                                     14
```

<210> SEQ ID NO 12
<211> LENGTH: 14
<212> TYPE: DNA
<213> ORGANISM: Artificial Sequence
<220> FEATURE:
<223> OTHER INFORMATION: Primer

<400> SEQUENCE: 12
acggagtgac aata                                                    14

<210> SEQ ID NO 13
<211> LENGTH: 14
<212> TYPE: DNA
<213> ORGANISM: Artificial Sequence
<220> FEATURE:
<223> OTHER INFORMATION: Primer

<400> SEQUENCE: 13
cttggttggt tttg                                                    14

<210> SEQ ID NO 14
<211> LENGTH: 14
<212> TYPE: DNA
<213> ORGANISM: Artificial Sequence
<220> FEATURE:
<223> OTHER INFORMATION: Primer

<400> SEQUENCE: 14
tggtgcttag aatc                                                    14

<210> SEQ ID NO 15
<211> LENGTH: 15
<212> TYPE: DNA
<213> ORGANISM: Artificial Sequence
<220> FEATURE:
<223> OTHER INFORMATION: Primer

<400> SEQUENCE: 15
ctacagattt tcctg                                                   15

<210> SEQ ID NO 16
<211> LENGTH: 15
<212> TYPE: DNA
<213> ORGANISM: Artificial Sequence
<220> FEATURE:
<223> OTHER INFORMATION: Primer

<400> SEQUENCE: 16
aggtgatcta ttggt                                                   15

<210> SEQ ID NO 17
<211> LENGTH: 14
<212> TYPE: DNA
<213> ORGANISM: Artificial Sequence
<220> FEATURE:
<223> OTHER INFORMATION: Primer

<400> SEQUENCE: 17
gcaagatttg tgac                                                    14

<210> SEQ ID NO 18
<211> LENGTH: 14
<212> TYPE: DNA
<213> ORGANISM: Artificial Sequence
<220> FEATURE:

```
<223> OTHER INFORMATION: Primer

<400> SEQUENCE: 18
gttttggtta cagg                                                          14

<210> SEQ ID NO 19
<211> LENGTH: 14
<212> TYPE: DNA
<213> ORGANISM: Artificial Sequence
<220> FEATURE:
<223> OTHER INFORMATION: Primer

<400> SEQUENCE: 19
gtgaagacga ggac                                                          14

<210> SEQ ID NO 20
<211> LENGTH: 15
<212> TYPE: DNA
<213> ORGANISM: Artificial Sequence
<220> FEATURE:
<223> OTHER INFORMATION: Primer

<400> SEQUENCE: 20
caatcacttc ttctg                                                         15

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
atagtcttcg gcgggcttc                                                     19

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cgatggaaat cctgcaccta                                                    20

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
cgtaataaac ttcaacagag cctaaa                                             26

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
ttctagttat gtaagagtgg tcctttc                                            27
```

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ttgtcactcc gttcaagtcg							20

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
gcctcaaaga gatttaactt cg						22

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
accagtcgca ttcaaaggag							20

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
tgaagtttcg caagaattga aa						22

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
gcgcttcgca atagttgt							18

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
ttgccagctt actatccttc ttg						23

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
catcaatgta tctaccaggc tca                                           23

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
aaattgactg ctggtgaagc                                               20

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
attttgaatg atgggtccc                                                19

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
agatttcaag ccacgtttgc                                               20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
tggcgtattt cgtatgacca                                               20

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
tgttgctgat aacctgtcga a                                             21

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
tggatggacg caaagaagtt                                               20

<210> SEQ ID NO 38
<211> LENGTH: 18

```
<212> TYPE: DNA
<213> ORGANISM: Artificial Sequence
<220> FEATURE:
<223> OTHER INFORMATION: Primer

<400> SEQUENCE: 38
gctcggcggc ttctaatc                                                 18

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
cgaatcaaat taacaaccat agga                                          24

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
aatacaaact gaaaatgttg aaagt                                         25

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
aaaaccaaag actgcggaat                                               20

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
tccgggttat agagttttgc tt                                            22

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
tgtcaataaa gtggaaatgt gtca                                          24

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
```

```
gaattttagg aatacaatgc agctt                                            25
```

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45

```
gaaaccaggc agttaataga aaaa                                             24
```

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46

```
gctgctgaaa aactaagaaa                                                  20
```

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47

```
ttaaaatcga ggcgaggtc                                                   19
```

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48

```
tgatttgttt gccgattacg                                                  20
```

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49

```
gcggctcgtg ctatattctt                                                  20
```

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50

```
ttgctgtata acgaatttta tgc                                              23
```

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
ccagcagaca agaaatcacc                    20

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
ttgagggtac ggagattatg g                   21

<210> SEQ ID NO 53
<211> LENGTH: 19
<212> TYPE: DNA
<213> ORGANISM: Artificial Sequence
<220> FEATURE:
<223> OTHER INFORMATION: Primer

<400> SEQUENCE: 53
attaacgccg ttattaacg                     19

<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54
ttcttggcta tgaaaatgag g                   21

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
gggaatctcg tagcatcacc                    20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
tgtgtgaccg aaaaggtctg                    20

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
tgttgtggaa atgtaaagag c                   21

```
<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
gcaatgagca gttaagcgta tt                                              22

<210> SEQ ID NO 59
<211> LENGTH: 24
<212> TYPE: DNA
<213> ORGANISM: Artificial Sequence
<220> FEATURE:
<223> OTHER INFORMATION: Primer

<400> SEQUENCE: 59
tttttagcct tatttctggg gtaa                                            24

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
aagtggttat gcagcttttc c                                               21

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
gctcattgtc ggtgtcgtta                                                 20

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
tccgaagtta aatctctttg agg                                             23

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
ttgctttgcc tctccttttg                                                 20

<210> SEQ ID NO 64
<211> LENGTH: 23
<212> TYPE: DNA
<213> ORGANISM: Artificial Sequence
<220> FEATURE:
<223> OTHER INFORMATION: Primer
```

-continued

```
<400> SEQUENCE: 64
cgtttggtaa agtagagggg gta                                           23

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
cgcaccataa tctccgtacc                                               20

<210> SEQ ID NO 66
<211> LENGTH: 19
<212> TYPE: DNA
<213> ORGANISM: Artificial Sequence
<220> FEATURE:
<223> OTHER INFORMATION: Primer

<400> SEQUENCE: 66
cgcttcacca gcagtcaat                                                19

<210> SEQ ID NO 67
<211> LENGTH: 21
<212> TYPE: DNA
<213> ORGANISM: Artificial Sequence
<220> FEATURE:
<223> OTHER INFORMATION: Primer

<400> SEQUENCE: 67
gggcctacta atccgtatgg t                                             21

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
tcccagaaga atgtcccctta g                                            21

<210> SEQ ID NO 69
<211> LENGTH: 22
<212> TYPE: DNA
<213> ORGANISM: Artificial Sequence
<220> FEATURE:
<223> OTHER INFORMATION: Primer

<400> SEQUENCE: 69
gaggaaaaat tggcagtaac ct                                            22

<210> SEQ ID NO 70
<211> LENGTH: 19
<212> TYPE: DNA
<213> ORGANISM: Artificial Sequence
<220> FEATURE:
<223> OTHER INFORMATION: Primer

<400> SEQUENCE: 70
gccccacaaa ccttcaaat                                                19

<210> SEQ ID NO 71
```

```
<211> LENGTH: 18
<212> TYPE: DNA
<213> ORGANISM: Artificial Sequence
<220> FEATURE:
<223> OTHER INFORMATION: Primer

<400> SEQUENCE: 71
atcaaagcca cgccaaac                                                 18

<210> SEQ ID NO 72
<211> LENGTH: 23
<212> TYPE: DNA
<213> ORGANISM: Artificial Sequence
<220> FEATURE:
<223> OTHER INFORMATION: Primer

<400> SEQUENCE: 72
cctacacgca aaggaactag aga                                           23

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
agcaaaccga acatcaaacc                                               20
```

METHODS OF DETECTING LONG RANGE CHROMOSOMAL INTERACTIONS

CROSS-REFERENCE TO RELATED APPLICATIONS

This application is a continuation application of National Phase application Ser. No. 12/995,261 filed Nov. 30, 2010, which is a claiming priority to PCT/GB2009/001377 filed Jun. 2, 2009 which claims priority under 35 U.S.C. § 119 to application GB 0810051.3 filed on Jun. 2, 2008, all of which are herein incorporated by reference in their entireties.

FIELD OF INVENTION

The current invention relates to methods of monitoring epigenetic changes, diagnosing specific physiological conditions and the use of antisense RNA for the treatment of physiological conditions.

BACKGROUND

The eukaryotic genome is organized into complex higher order structures; in fact, early electron micrographs of extracted chromatin revealed a non-histone scaffold forming radial loops (Earnshaw and Laemmli, 1983, J Cell Bio 96, 84-93). Unrestrained negative superhelicity in mammalian genomes suggests chromosome "domain" sizes on the order of tens of kilobases (Kramer and Sinden, 1997, Biochem 36, 3151-3158). More recently, using 3C technology (chromosome conformation capture) higher order long range interactions have been demonstrated to exist in a wide variety of eukaryotes including *S. cerevisiae* (Dekker et al, 2002, Science 295, 1306-1311), fly (Blanton et al, 2003 Genes Dev 17, 664-675), mouse (Tolhuis et al, 2002, Mol Cell 10, 1453-1465) and human (Carroll et al, 2005, Cell 122, 33-43) cells, generally kilobases in size. In mammalian cells, association of enhancer or locus control regions with actively expressed genes has been demonstrated in the β-globin (Tolhuis et al, 2002, Mol Cell 10, 1453-1465) and C-reactive protein (Choi et al, 2007, Nucleic Acids Res 35, 5511-5519) loci, as well as looping together of recombining immunoglobulin genes (Skok et al, 2007, Nat Immunol 8, 378-387). In mammalian cells, ongoing transcription is proposed to drive genome organization and gene looping (Chakalova et al, 2005 Nat Rev Genet 6, 669-677; Marenduzzo et al, 2007, Trends Genet 23, 126-133 and references therein) but recent analyses suggest that, at least for the β-globin locus, some long range DNA interactions are maintained after transcription is inhibited (Palstra et al, 2008 PLoS ONE 3, e1661) arguing against models suggesting that engaged RNA polymerase functions as ties of chromatin loops.

In the yeast genome, active transcription does appear to be important for the formation of "gene loops", long range interactions that link the 5' and 3' regions of active genes (Ansari and Hampsey, 2005 Genes Dev 19, 2969-2978, O'Sullivan et al, 2004, Nat Genet 36, 1014-1018; Singh and Hampsey, 2007, Mol Cell 27, 806-816). Chromatin immunoprecipitation (ChIP) demonstrates the presence of TFIIB and the phosphorylated form of RNAPII on both promoters and terminators. Moreover, functional TFIIB is required to form these long range interactions (Singh and Hampsey, 2007, Mol Cell 27, 806-816). TFIIB is capable of interacting with non-coding RNA and loss of TFIIB promoted by the non-coding RNA leads to loss of long range interaction at DFHR (Martianov et al, 2007, Nature 445, 666-670).

High levels of non-coding RNA transcribed throughout the genome include transcripts antisense to open reading frames. They feature in both eukaryotic and prokaryotic genomes (Johnson et al, 2005, Trends Genet 21, 93-102, Kapranov et al, 2007, Nat Rev Genet 8, 413-423; Selinger et al, 2000, Proc Natl Acad Sci USA 103, 4192-4197). In eukaryotes, many of these transcripts are never destined for translation into protein and some are targeted for exosome-mediated degradation by the TRAMP complex (Bickel and Morris, 2006 Mol Cell 22, 309-316). In yeast these cryptic unstable transcripts (CUTs) are detected at promoters (Berretta et al, 2008, Genes Dev 22, 615-626; Davis and Ares, 2006, Proc Natl Acad Sci USA 103, 3262-3267), in intergenic regions (Wyers et al, 2005, Cell 121, 725-737) and antisense to genes (Camblong et al, 2007 Cell 131, 706-717; Uhler et al, 2007, Proc Natl Acad Sci USA 104, 8011-8016).

Detailed experiments profiling RNAs from *S. cerevisiae* using genomic tiling arrays have shown that transcription occurs in virtually all parts of the yeast genome (Perocchi et al, 2007, Nucleic Acids Res 35, e128; Samanta et al, 2006, Proc Natl Acad Sci USA 103, 4192-4197; Miura et at et al, 2006, PNAS 103, 17846-17851; Hongay et al, 2006, Cell 127, 735-745; David et al, 2006, Proc Natl Acad Sci USA 103, 5320-5325; Havilio et al, 2005, BMC Genomics 6, 93). These analyses also indicate that between 100 and 370 genes are transcribed at least partially in both directions producing stable polyadenylated sense and antisense transcripts. Many of these genes are actively transcribed.

The current inventors have used the GAL locus as a model system in which to compare induced and repressed states and observe differences in antisense transcript and epigenetic regulation. The inventors show that there are antisense transcripts controlling both the induced and repressed states at the GAL locus, and that these transcripts differ in size, position and abundance. Highly abundant antisense transcripts at the induced locus are associated with the production of the sense transcript from the GAL10 promoter. Moreover, the levels of antisense transcripts strongly correlate with levels of Hda1 associated with the locus but not with histone acetylation itself. The inventors also identify that Hda1 appears to be required for long range interactions at the repressed GAL locus, suggesting a link between the antisense transcripts, epigenetic modifications and higher order chromatin structures in the repressed state. Changes in the conformation of the locus upon switching from the repressed to the induced state have been identified with implication of antisense RNA in controlling this. The current invention is based on the discovery that gene repression is a proactive state of regulation which involves production of antisense transcription and specific epigenetic changes the locus.

SUMMARY

According to a first aspect of the invention there is provided a method of monitoring epigenetic changes comprising monitoring changes in conditional long range chromosomal interactions at at least one chromosomal locus where the spectrum of long range interaction is associated with a specific physiological condition, said method comprising the steps of:—
(i) in vitro crosslinking of said long range chromosomal interactions present at the at least one chromosomal locus;
(ii) isolating the cross linked DNA from said chromosomal locus;

(iii) subjecting said cross linked DNA to restriction digestion with an enzyme that cuts at least once within the at least one chromosomal locus;
(iv) ligating said cross linked cleaved DNA ends to form DNA loops;
(v) identifying the presence of DNA loops;
wherein the presence of DNA loops indicates the presence of a specific long range chromosomal interaction.

It will be understood that conditional long range chromosomal interactions will always be present in chromatin. It will be further understood that these interactions are dynamic and will change depending on the status of the region of the chromosome, i.e. if it is being transcribed or repressed in response to change of the physiological conditions As used herein, the term conditional long range interactions refers to interactions between distal regions of a locus on a chromosome, said interactions being dynamic and altering depending upon the status of the region of the chromosome.

As used herein, the term spectrum of long range interaction refers to the different conformations of long range chromosomal interactions which may be present at a given chromosomal locus. It will be understood that as described above these interactions are dynamic, with various long range interactions forming or breaking depending on the status of the locus.

It will further be understood that the long range chromosomal interactions can be cross linked by any suitable means. In a preferred embodiment, the long range chromosomal interactions are crosslinked using formaldehyde.

It will be further understood that the DNA loops present may be indicative of transcription or repression of said chromosomal locus, or alternatively, expression of an altered product from said chromosomal locus.

The presence of the DNA loops can be identified as described herein below in relation to the GAL locus. It will be readily apparent to the skilled person that the method described in relation to this locus can be adapted to be used at any other locus where long range interactions are thought to occur. These loops can be detected using techniques known in the art such as the 3C (chromosome conformation capture) assay (Dekker, 2006, Nat Methods 3, 17-21; Dekker et al, 2002, Science 295, 1306-1311; O'Sullivan et al, 2004, Nat Genet 36, 1014-1018).

The skilled person will be aware of numerous restriction enzymes which can be used to cut the DNA within the chromosomal locus of interest. It will be apparent that the particular enzyme used will depend upon the locus studied and the sequence of the DNA located therein.

The current invention is based on the surprising discovery by the inventors that conditional long range chromosomal interactions are always present at a given locus on the chromosome and that the profile of conditional long range chromosomal interactions change depending on the actual status of the region, it's activity and the physiological conditions, i.e. the presence or absence of a particular long range interaction will provide an indication of the status of that region.

Moreover, the inventors have discovered that consistent with earlier genetic data these conditional long range chromosomal interactions may overlap and include the regions of chromosomes shown to encode relevant or undescribed genes, but equally may be in intergenic regions. It should further be noted that the inventors have discovered that long range interactions in all regions are equally important in determining the status of the chromosomal locus. These long range interactions are not necessarily in the coding region of a particular gene located at the locus and may be in intergenic regions.

It will further be understood by the skilled person that the term epigenetic refers to heritable changes in gene function within a cell which are caused by changes other than changes to the underlying DNA sequence, these changes may be caused, for example, by environmental factors, DNA methylation, non-coding antisense RNA transcripts, non mutagenic carcinogens, histone modifications, chromatin remodelling and specific local long range DNA interactions all of which have been implicated in creating specific environment for defined transcriptional activity on the genes or non-coding RNA transcriptional units within the region of interest.

It will be understood that the epigenetic changes may be caused by changes to the underlying nucleic acid sequence, which themselves do not directly effect a gene product or the mode of gene expression, such changes may be for example, SNP's within and/or outside of the genes, and gene fusions and/or deletions of intergenic DNA.

It will further be apparent that the term specific physiological condition refers to any condition in which there is a change in the defined physiological status of the cell. This may be by a change in the level of expression of one or more genes, or a change in one or more gene product. Examples of such conditions include cancer—benign or malignant growth, cardiovascular disorders, inflammatory conditions, including autoimmune disorders and inflammatory responses to the developing infectious diseases, inherited genetic disorders modulated by epigenetic mechanisms and neurodegenerative diseases.

Preferably, the presence of the DNA loops is identified using PCR techniques. It will be understood that the presence of a loop may be indicated by the presence of a PCR product which is absent in the absence of DNA loop or vice versa. It will also be understood that the size of the PCR product produced may be indicative of the specific DNA loop present and may therefore be used to identify the status of the locus.

In one preferred embodiment, the presence of a DNA loop indicates an altered transcription state indicative of a specific physiological condition.

In a second preferred embodiment, the absence of a DNA loop indicates an altered transcription state indicative of a specific physiological condition.

It will be apparent to the skilled person that the method according to the first aspect can be used not only to monitor the presence of a specific long range chromosomal interaction at a chromosomal locus, but equally to monitor the absence of a specific long range chromosomal interaction at said chromosomal locus.

Preferably, the physiological condition is selected from amongst cancer, cardiovascular disorders, inflammatory conditions, including autoimmune disorders and inflammatory responses to infectious diseases, and inherited genetic disorders modulated by epigenetic mechanisms. Any other condition which results in a change in at least one long range chromosomal interaction may also be identified by the currents methods.

It will be understood that in any aspect of the present invention the changes in the conditional long range chromosomal interactions of a sample may be monitored by comparing the conformation of long range chromosomal interactions at a locus at different time points in the same tissue or cell type or by comparison to a sample corresponding to a known physiological state.

Furthermore, it should be understood that the long range chromosomal interactions of the present invention do not relate to long range interactions between genes and their regulatory elements such as previously described by Chambeyron et al., (2004), Curr Opin Biol. 16, 256-262; de Laat et al., (20030 Chromosome res. 11, 447-459; and Dekker, (2003), J. Trends Biochem. Sci. 28, 277-280. Rather the present invention relates to conditional changes in the long range interactions within a particular locus as an indication of a switch in the activity of a gene.

According to a second aspect of the current invention there is provided a method of monitoring epigenetic changes comprising monitoring changes in conditional long range chromosomal interactions at at least one chromosomal locus where the spectrum of long range interaction is associated with a specific physiological condition, said method comprising the step of identifying a change in the antisense RNA profile expressed from the at least one chromosomal locus.

It will be apparent to the skilled person that the change in the antisense RNA profile may be a change in the size, start position, and/or number of antisense RNA transcripts.

It will be understood by the skilled person that the phenomenon of the production of antisense RNA transcripts at repressed loci on chromosomes is known. However, the inventors have surprisingly discovered that the profile of antisense RNA transcribed from a chromosomal locus changes depending on whether the locus is induced or repressed and that the antisense RNA transcripts produced play a central role in controlling transcription of the sense RNA transcript from a particular locus and the epigenetic conditions at that locus, including the long range interactions.

According to a third aspect of the current invention there is provided a method of diagnosing a disorder associated with at least one epigenetic change in a subject, said method comprising identifying a change in one or more long range chromosomal interactions at at least one chromosomal locus associated with said disorder in a sample isolated from the subject; wherein said method comprises the method of either of aspects one or two.

Preferably, the epigenetic change results in altered transcription from the chromosomal locus.

It will be understood that the altered transcription can be up regulation, repression, or production of an alternative transcript with a changed start site and/or termination site, or a splice variant of such.

It will be apparent that the epigenetic change causes a change in the expression of at least one gene and/or transcriptional unit within the non-coding part of the genome.

Preferably, the disorder is selected from amongst cancer, cardiovascular disorders, inflammatory conditions, including autoimmune disorders and inflammatory responses to infectious diseases, and inherited genetic disorders modulated by epigenetic mechanisms. Any other condition which results in a change in at least one long range chromosomal interaction may also be diagnosed by the currents methods.

According to a fourth aspect of the current invention there is provided a method of regulating transcription of at least one gene in a patient suffering from a disorder associated with altered gene expression, said method comprising administering to said patient an antisense RNA in an amount effective to alter transcription of said at least one gene.

In one embodiment, the disorder results from over expression of said at least one gene.

It will be apparent to the skilled person that the disorder can equally result from repression of said at least one gene, or from production of an altered gene product from said at least one gene.

Preferably, the disorder is selected from amongst cancer, cardiovascular disorders, inflammatory conditions, including autoimmune disorders and inflammatory responses to infectious diseases, and inherited genetic disorders modulated by epigenetic mechanisms.

In a preferred embodiment, said antisense RNA targets at least one CTCF binding site.

CTCF is a multifunctional factor, which as discussed below is implicated in establishing and maintaining high order chromatin structures.

In a further preferred embodiment, administration of said antisense RNA results in modulation of HDAC enzymes.

Histone acetylation is known to be involved with modulation of transcription. It has been suggested that this modulation is also controlled via antisense RNA.

HDAC enzymes are classified into four classes depending on sequence identity and domain organization. In a preferred embodiment, said HDAC enzyme is selected from a Class i-iv HDAC enzyme.

Class I HDAC enzymes include HDAC1, HDAC2, HDAC3, HDAC8; Class II HDAC enzymes include HDAC4, HDAC5, HDAC6, HDAC7A, HDAC9, HDAC10; Class III HDAC enzymes include homologs of Sir2 in the yeast *Saccharomyces cerevisiae*, and sirtuins in mammals (SIRT1, SIRT2, SIRT3, SIRT4, SIRT5, SIRT6, SIRT7); Class IV HDAC enzymes include HDAC 11.

According to a fifth aspect of the current invention there is provided a method of regulating transcription of at least one gene in a patient suffering form a disorder associated with altered gene expression, said method comprising administering to said patient interfering RNA complementary to an antisense RNA molecule implicated in modulation of said gene.

It will be apparent to the skilled person that the disorder can result from over expression or repression of said at least one gene, or from production of an altered gene product from said at least one gene.

Preferably, the disorder is selected from amongst cancer, cardiovascular disorders, inflammatory conditions, including autoimmune disorders and inflammatory responses to infections diseases, and inherited genetic disorders modulated by epigenetic mechanisms.

According to a sixth aspect of the current invention, there is provided antisense RNA for the treatment of a disorder associated with altered gene expression, wherein said antisense RNA regulates transcription of said gene.

According to a seventh aspect there is provided the use of antisense RNA in the manufacture of a medicament for the treatment of a disorder associated with altered gene expression, wherein said antisense RNA regulates transcription of said gene.

Preferably, the disorder according to the fifth or sixth aspect is selected from amongst a cancer, cardiovascular disorders, inflammatory conditions, including autoimmune disorders and inflammatory responses to infectious diseases, and inherited genetic disorders modulated by epigenetic mechanisms.

In a first preferred embodiment, said RNA represses transcription of said gene.

In a second preferred embodiment, said RNA induces transcription of said gene.

In a preferred embodiment, said antisense RNA targets at least one CTCF binding site.

In a further preferred embodiment, said antisense RNA modulates HDAC enzymes.

It will be apparent to the skilled person that the above medicaments may be formulated into pharmaceutical dosage forms, together with suitable pharmaceutically acceptable carriers, such as diluents, fillers, salts, buffers, stabilizers, solubilisers, etc. The dosage form may contain other pharmaceutically acceptable excipients for modifying conditions such as pH, osmolarity, taste, viscosity, sterility, lipophilicity, solubility etc.

Suitable dosage forms include solid dosage forms, for example, tablets, capsules, powders, dispersible granules, cachets and suppositories, including sustained release and delayed release formulations. Powders and tablets will generally comprise from about 5% to about 70% active ingredient. Suitable solid carriers and excipients are generally known in the art and include, e.g. magnesium carbonate, magnesium stearate, talc, sugar, lactose, etc. Tablets, powders, cachets and capsules are all suitable dosage forms for oral administration.

Liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Suitable diluents and solvents include sterile water, Ringer's solution and isotonic sodium chloride solution, etc. Liquid dosage forms also include solutions or sprays for intranasal administration.

Aerosol preparations suitable for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations may be conveniently prepared in unit dosage form, according to standard procedures of pharmaceutical formulation. The quantity of active compound per unit dose may be varied according to the nature of the active compound and the intended dosage regime.

The active agents are to be administered to human subjects in "therapeutically effective amounts", which is taken to mean a dosage sufficient to provide a medically desirable result in the patient. The exact dosage and frequency of administration of a therapeutically effective amount of active agent will vary, depending on such factors as the nature of the active substance, the dosage form and route of administration.

According to a eighth aspect of the current invention there is provided a method of identifying the transcription status of a chromosomal locus, said method comprising the steps of; identifying the antisense RNA transcript profile expressed from said chromosomal locus; and comparing said profile with the antisense RNA transcript profile of said chromosomal locus in a known state.

Preferably, said chromosomal locus comprises at least one gene.

Preferably, said gene is a gene known or suspected of being involved in a specific physiological condition.

It will be understood that said condition can be any condition associated with an epigenetic change, for example, cancer, cardiovascular disorders, inflammatory conditions, including autoimmune disorders and inflammatory responses to infectious diseases, and inherited genetic disorders modulated by epigenetic mechanisms.

Preferably, said method is performed in vitro.

For the avoidance of doubt, it is stated that features described in relation to one aspect of the invention are equally applicable to all other aspects of the invention. Furthermore, where a number of features are indicated as options, each individual feature is contemplated as being applicable individually or in combination with any other feature described in the application.

The invention will now be further described with reference to the following examples and figures in which:—

FIG. 1. Conditional antisense transcripts at GAL10
Northern blots of total RNA probed with sense and antisense specific probes at GAL10. A, B. Strain BY4741 was culture in galactose (lane 1), washed (lane 2) and transferred to medium containing glucose for 15 minutes (lane 3), 60 minutes (lane 4), 120 minutes (lane 5), 180 minutes (lane 6) or 360 minutes (lane 7). Two exposures of the antisense signal in B are shown. The position of the rRNA bands is indicated. The left panel in B and panel A were exposed for the same time. At 15 minutes the 2.25 kb and the 2.4 kb GAL10 AS (see FIG. 3B) are both detectable as the switch from the active to the repressed state occurs. C. Yeast cultured overnight in galactose were washed and transferred to fresh medium containing the sugar indicated. In this experiment, high levels of the GAL10 and GAL10-7 fusion transcript are evident in galactose with the equivalent antisense transcripts. The sense exposure is 20% of the antisense. Twice as much RNA is loaded in lane 2*.

Figure 2:
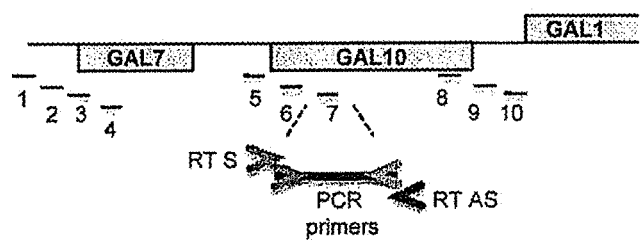
Figure 2:
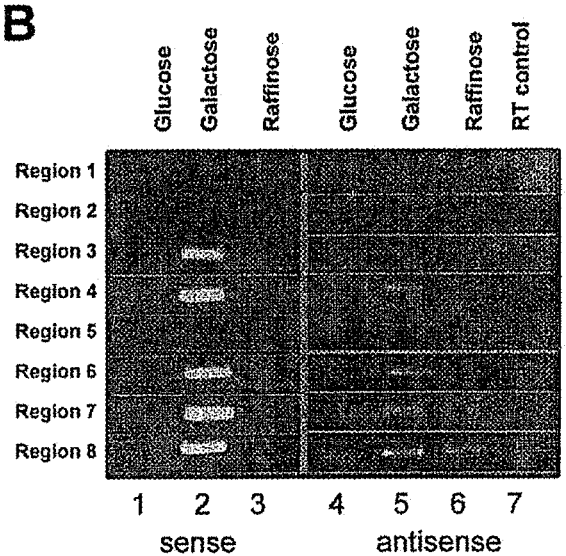
Figure 2:
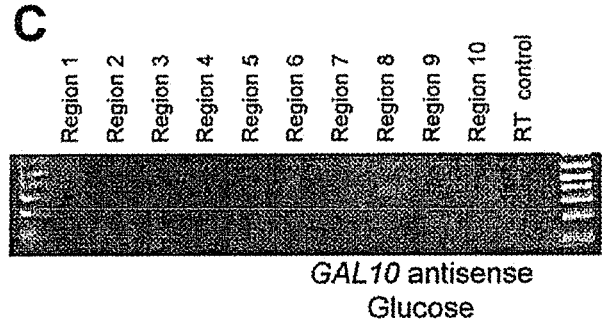

FIG. 2. Reverse transcription (RT)-PCR mapping transcripts at the GAL locus A Position of RT primers for reverse transcription (RT) of the sense (S) or antisense (AS) transcript and nested primers for PCR amplification. Each set of primers is designed to amplify a region about 200-300 bp at the sites shown at the GAL locus. B Mapping sense and antisense transcripts in total RNA in three carbon sources across GAL7 and GAL10. The control lacking RTase for the RNA prepared in glucose is shown in lane 7. C Mapping antisense transcripts at GAL7 and GAL10 in total RNA prepared from cells grown in glucose. Controls include omitting the RT step and a positive control for PCR primer efficiency on total DNA (not shown).

Figure 3:
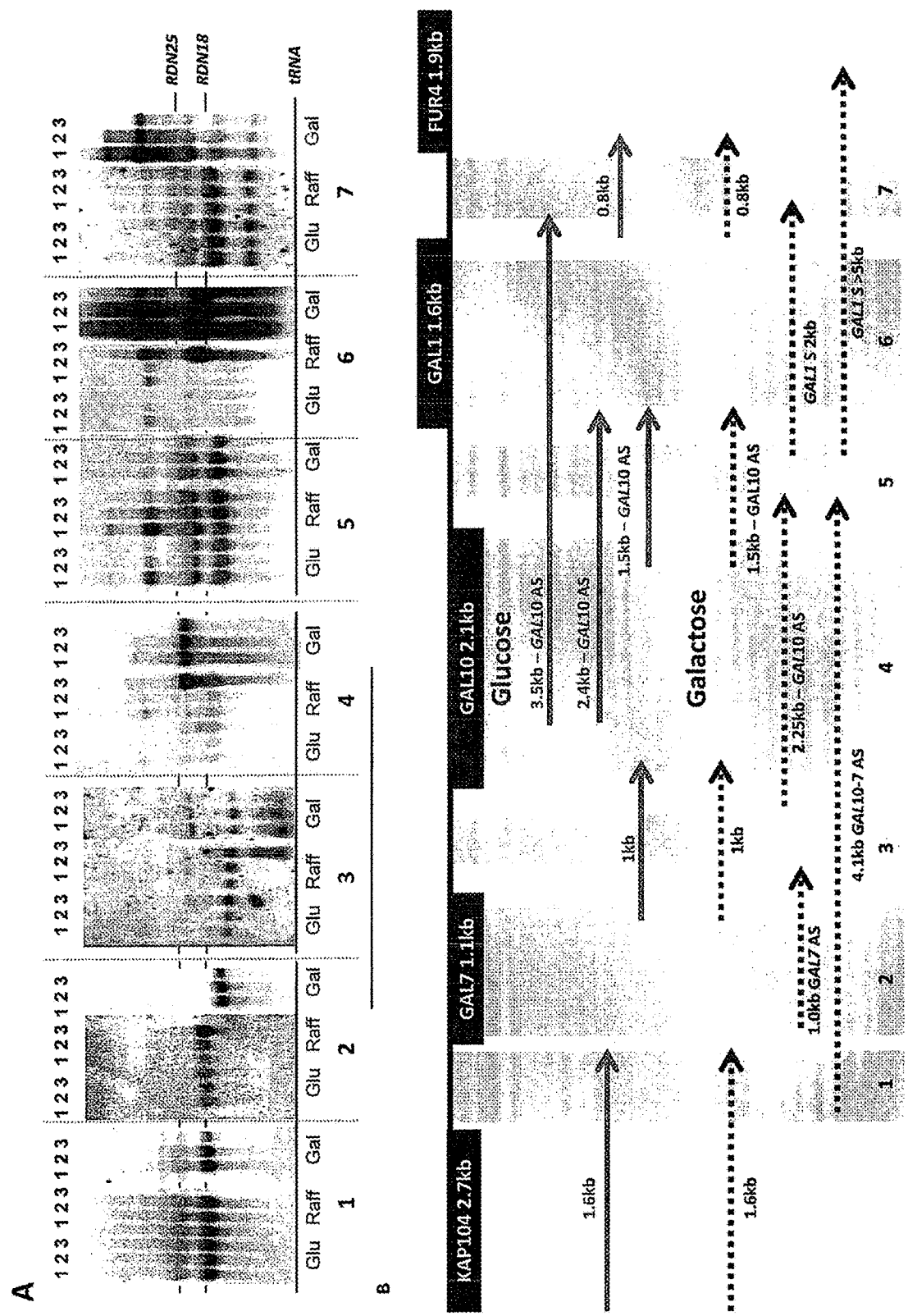

FIG. 3. Mapping transcripts at the GAL locus with strand-specific probes. A Autoradiographs of total RNA prepared from BY4741 (lane 1), W303-1a (lane 2) and YMH147 (lane 3) cultured in glucose, raffinose or galactose and hybridized to single strand specific probes 1-7 (all designed to detect antisense transcripts with respect to GAL10). The positions of the rRNAs (RDN25 and RDN18) and tRNA are marked with black lines across the autoradiographs, which were exposed for 24 hours. B Summary of data in FIG. 2 and FIG. 3A showing transcripts at repressed (glucose) or induced (galactose) locus.

Figure 4:
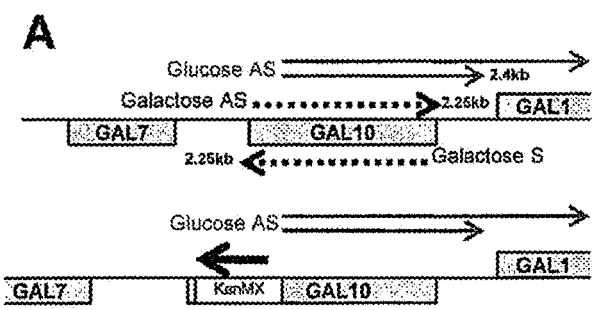
Figure 4:
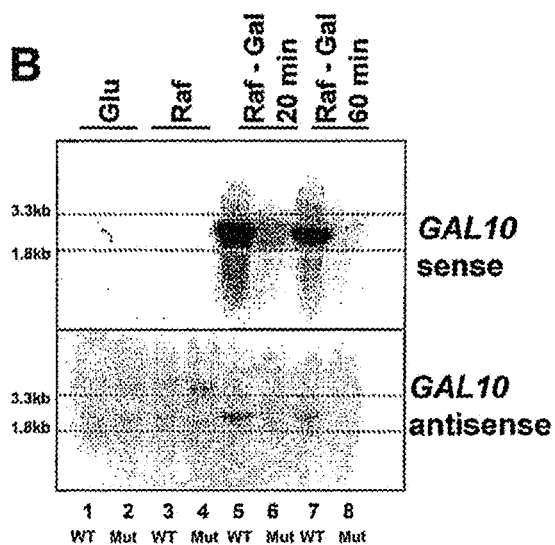
Figure 4:
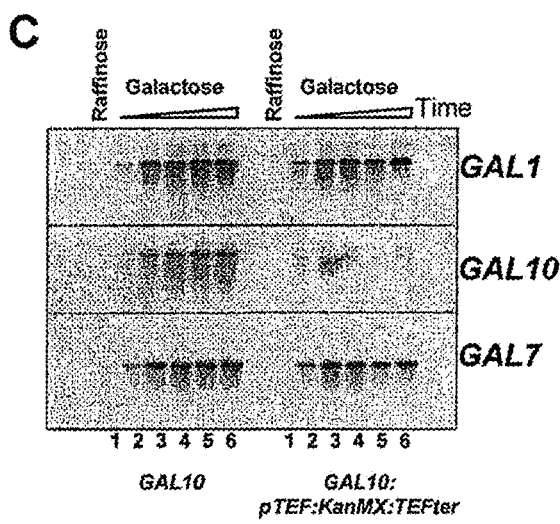

FIG. 4. Sequences at the 3' end of GAL10 are required for induction of the sense transcript. A Schematic showing the position of the major transcripts at repressed or induced GAL10 (WT) and a derivative of GAL10 containing a pTEF:KanMX:TEFter (Mut) insertion creating a deletion of 554 bp at the 3' end of GAL10. B and C Northern blots of total RNA from the strains shown cultured in the carbon sources indicated. In B the position of the rRNAs is indicated with dotted lines and sense and antisense specific probes were used. The autoradiographs were exposed for equivalent times. In C cultures were induced and samples prepared at 10 minutes intervals after transfer from raffinose (lane 1) to galactose (lanes 2-6).

Figure 5:
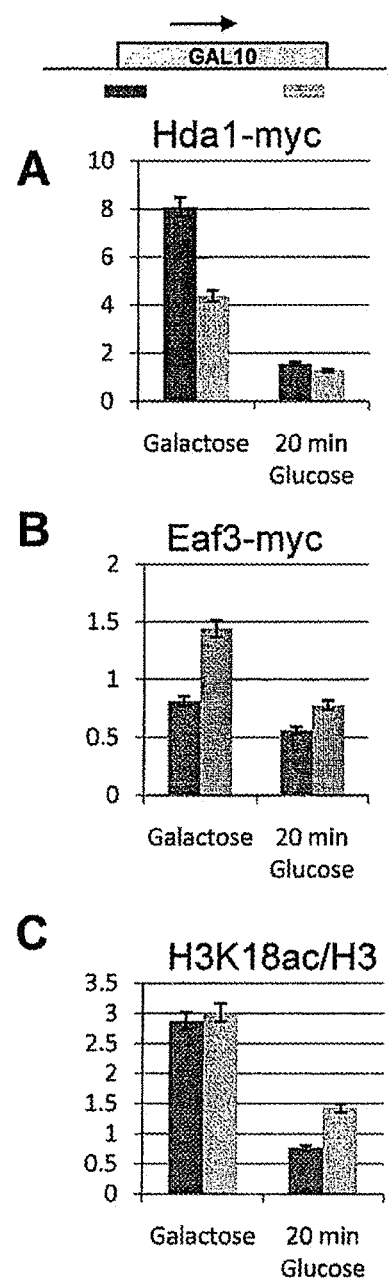

FIG. 5. Hda1 and Eaf3 association with GAL10 is related to levels of antisense transcript. Immunoprecipitation of chromatin prepared from cells cultured overnight in galactose and transferred to fresh medium containing galactose or glucose for 20 minutes and detected using real time PCR at GAL10. A Hda1-myc normalized to the untagged control. B Eaf3 normalized to the untagged control. C H3K18ac normalized to H3K18R and then histone H3

Figure 6:
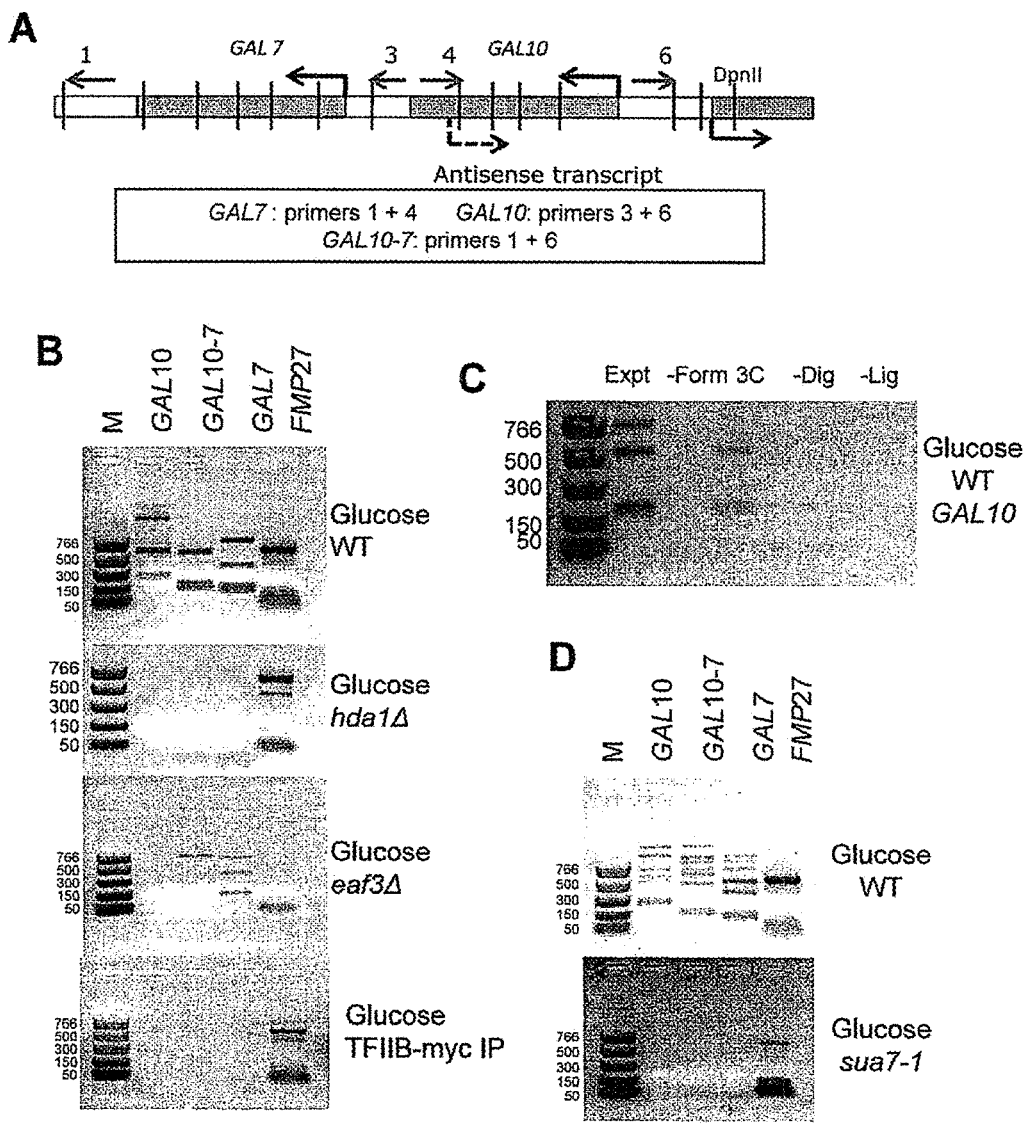

FIG. 6. 3C with immunoprecipitation at the repressed GAL locus. A Map of DpnII restriction sites (vertical lines) showing the number, position and orientation of primers (arrows 3' H) and the approximate position of the induced sense transcripts and the antisense transcript at the repressed locus. B 3C with IP (Rbp1 top three panels, Myc bottom panel) in the strains shown (BY4741 background) at the sites indicated. C Controls for the standard reaction for including no formaldehyde crosslinking (-Form), no digestion (-dig), no DNA ligase, no ATP (-lig). On the gel is a 3C product (-IP step) and the standard 3C with immunoprecipitation (Expt). PCR products for the long range interaction at GAL10 are shown. All other interactions showed similar dependencies (not shown). D 3C with IP (Rbp1) in the strains shown (BY4741 background) at the sites indicated.

Figure 7:
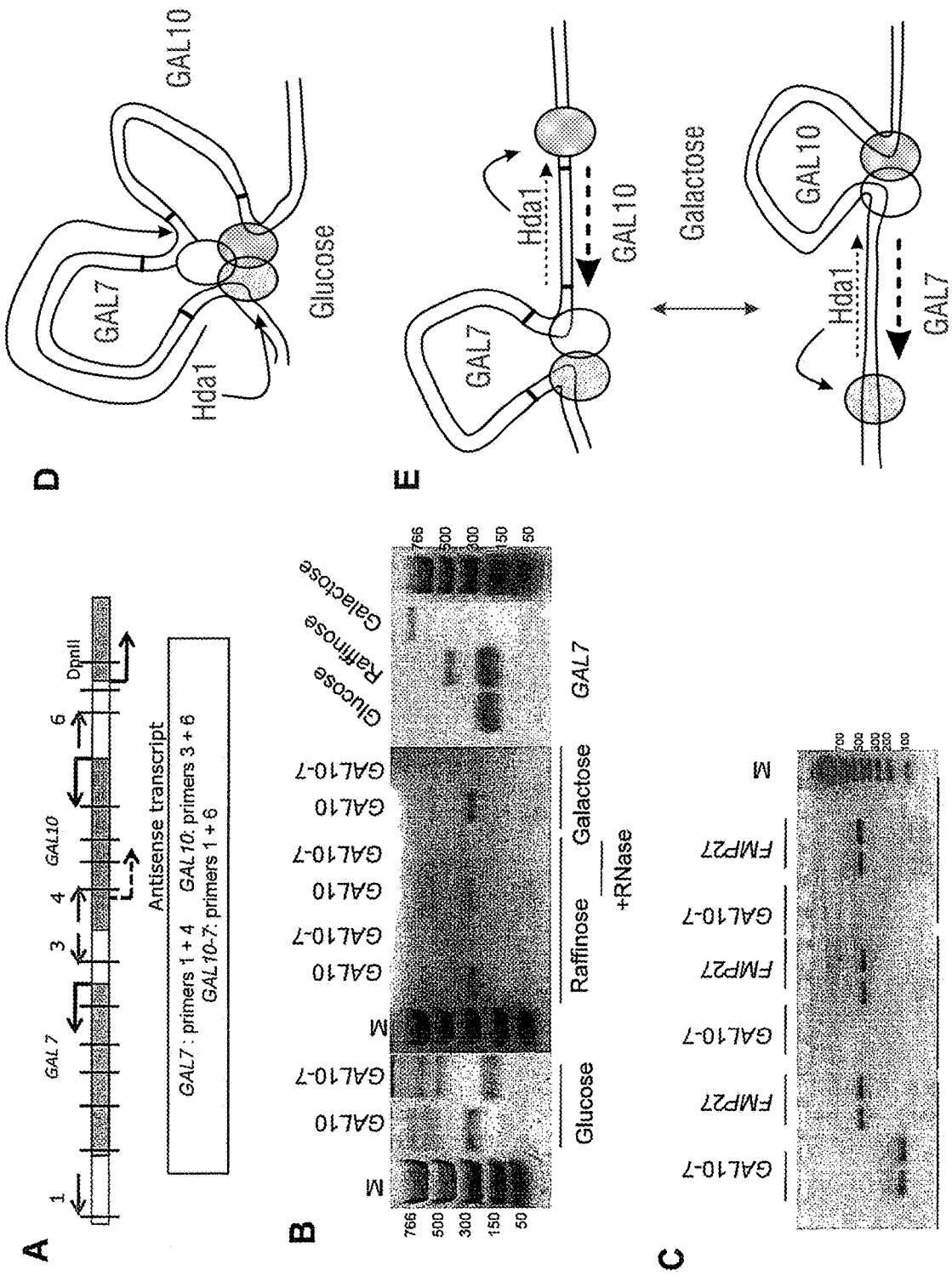

FIG. 7. Conditional long range interactions at the GAL locus. A Map of DpnII restriction sites (vertical lines) showing the number, position and orientation of primers (arrows 3'OH) and the approximate position of the induced sense transcripts and the antisense transcript at the repressed locus. B 3CIP (Rbp1) products at the sites indicated from chromatin isolated from BY4741 cells grown in the carbon sources indicated. C 3C IP (Rbp1) over GAL10-7 and FMP27 in the WT strain (BY4741 background) grown in three different carbon sources. D A model for dynamic long range interactions at the repressed locus. The antisense transcripts from GAL7 (shown), GAL10 and other non-coding transcripts at the intergenic regions, together with the Hda1 and Eaf3 lysine deacetylases are proposed to create an environment suitable for long range interactions. In glucose, interactions across GAL10, GAL7 and GAL10-7 are detectable and a model to accommodate this is shown. Given their association with RNAPII and TFIIB, the long range interactions appear to represent a poised but repressed state with no active transcription at the locus. E A model for conditional long range interactions at the GAL locus. As at the repressed locus, long range interactions appear to represent a poised non-active state over the genes. An increase in dynamic switching involving long range interactions at GAL10 and GAL7 when glucose repression is removed (i.e. in raffinose) would lead to loss of the long range interaction over GAL10-l-7. The onset of active transcription would contribute to dynamic switching between expressed and repressed states. The production of the antisense transcripts at the induced locus is envisaged to play two roles: to facilitate production of the sense transcript and through Eaf3 and Hda1 to prime the region for repression and the formation of long range interactions when the gene is not actively expressed.

Figure 8:
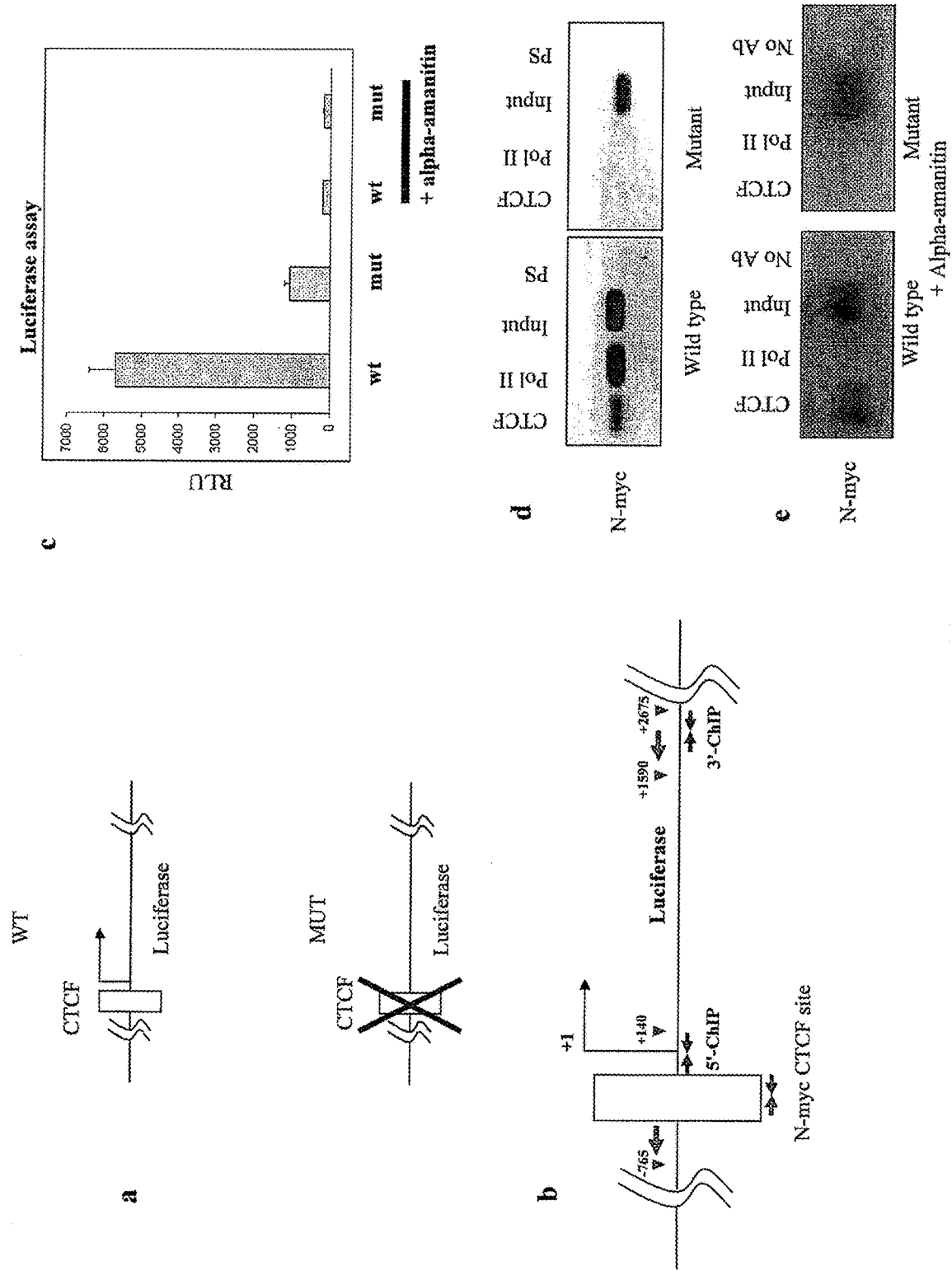

FIG. 8. In vivo CTCF-dependent transcriptional system. a, The integrated Luciferase reporter gene contains the wild type 90 bp CTCF-binding site N-Myc (pN-MycLuc wt) or a mutant deficient for CTCF binding (pN-MycLuc wt), in place of the promoter [13]. b, The enlarged map of the integrated construct with the positions of the primers indicated. Primers for ChIP assays at the N-Myc sites are shown in red and described previously [13]. Primers at the 5' are depicted in brown, at the 3' ends in blue; primers used in 3C and 4C assays are indicated in green. These primers are described under Materials and Methods in the on-line Supplement. The relevant TaqI restriction sites are shown as pale blue triangles; their positions are marked in relation to the Luciferase transcription start site. c, Presence of the wild type CTCF binding site is sufficient to drive the expression of Luciferase in pN-MycLuc wt; treatment with alpha-amanitin dramatically reduces the activity of Luciferase. d, CTCF and Pol II are bound to the N-Myc site in pN-MycLuc wt, but not in pN-MycLuc mut, as shown by ChIP assay with the indicated antibodies. e, Treatment with alpha-amanitin leads to dissociation of Pol II, but not CTCF from the N-Myc site, as shown by ChIP assay with the indicated antibodies. In panels "d" and "e", primers used for the analysis are shown in red in FIG. 1b and described earlier [13].

Figure 9:
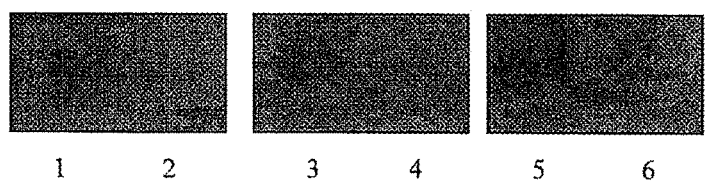
Figure 9:
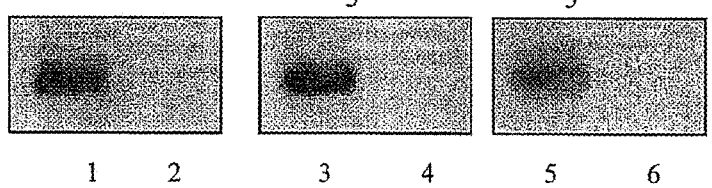
Figure 9:
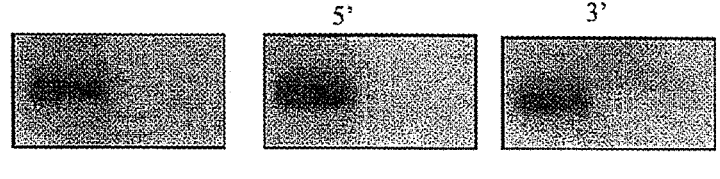

FIG. 9. Chromatin Conformation Capture (3C) and ChIP assays. a, The 5' and 3' ends (green arrows in FIG. 1b) are juxtaposed in pN-MycLuc wt (Lane 3), but not in N-MycLuc mut (Lane 4) as revealed by the 3C assay. Lane 1 is the positive control for the ligated template, Lane 2 is the negative ligation control. Primers used for the analysis are described under Materials and Methods in the on-line Supplement. b, The 5' (Lane 3) and 3' (Lane 5) sites of pN-MycLuc wt, but not pN-MycLuc mut (Lanes 4 and 6), are occupied by Pol II, as revealed by the ChIP assay with the anti-Pol II antibody. Lane 1—input, Lane 2—preimmune serum; c, The 5' (Lane 3) and 3' (Lane 5) sites of pN-MycLuc wt, but not pN-MycLuc mut (Lanes 4 and 6), are occupied by CTCF. Lane 1—input, Lane 2—preimmune serum. In panels "b" and "c" the 5'-end specific primers are shown in brown and the 3'-end specific primers are shown in blue.

Figure 10:
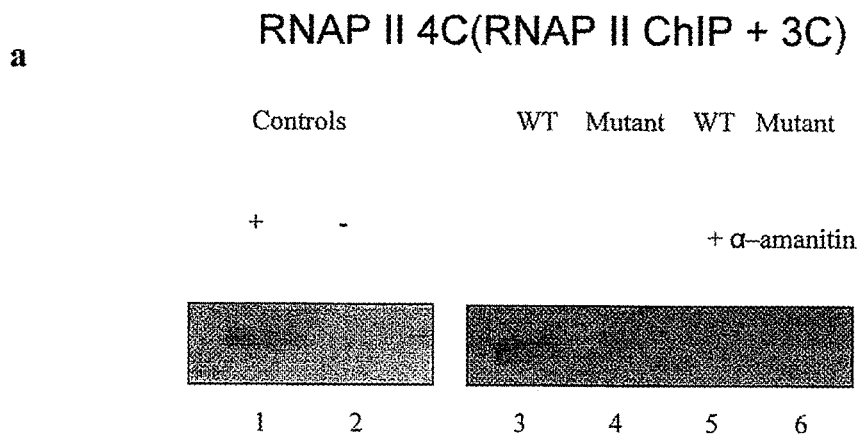
Figure 10:
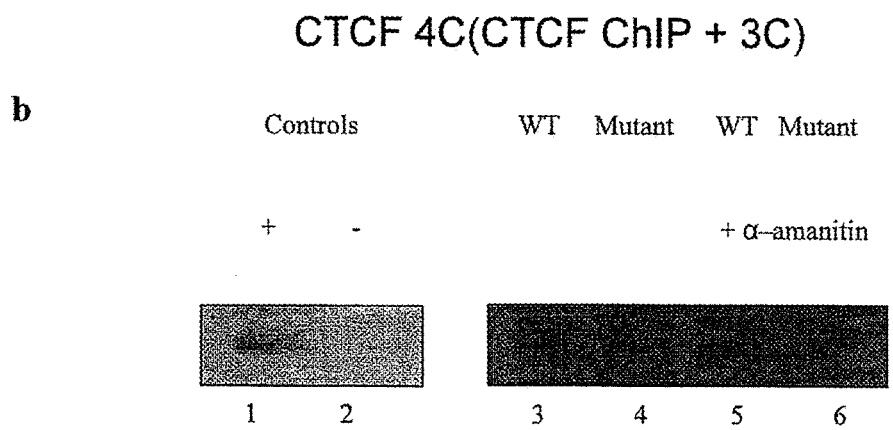

FIG. 10. The 4C assay (combination of ChIP and 3C assay) with the anti-Pol II and CTCF antibodies. Primers used for the analysis are shown in green in FIG. 1b and described under Materials and Methods in the on-line Supplement. a, Pol II is present at the juxtaposition of the 5' and 3' sites of the pN-MycLuc wt (Lane 3), but not of the pN-MycLuc mut (Lane 4). treatment with alpha-amanitin leads to the disappearance of Pol II from the high order chromatin structures in pN-MycLuc wt (lane 5). b, CTCF is present at the juxtaposition of the 5' and 3' sites of the pN-MycLuc wt (Lane 3), but not of the pN-MycLuc mut (Lane 4). CTCF is still associated with the high order chromatin structure in pN-MycLuc wt following treatment with alpha-amanitin (Lane 5).

Figure 11:
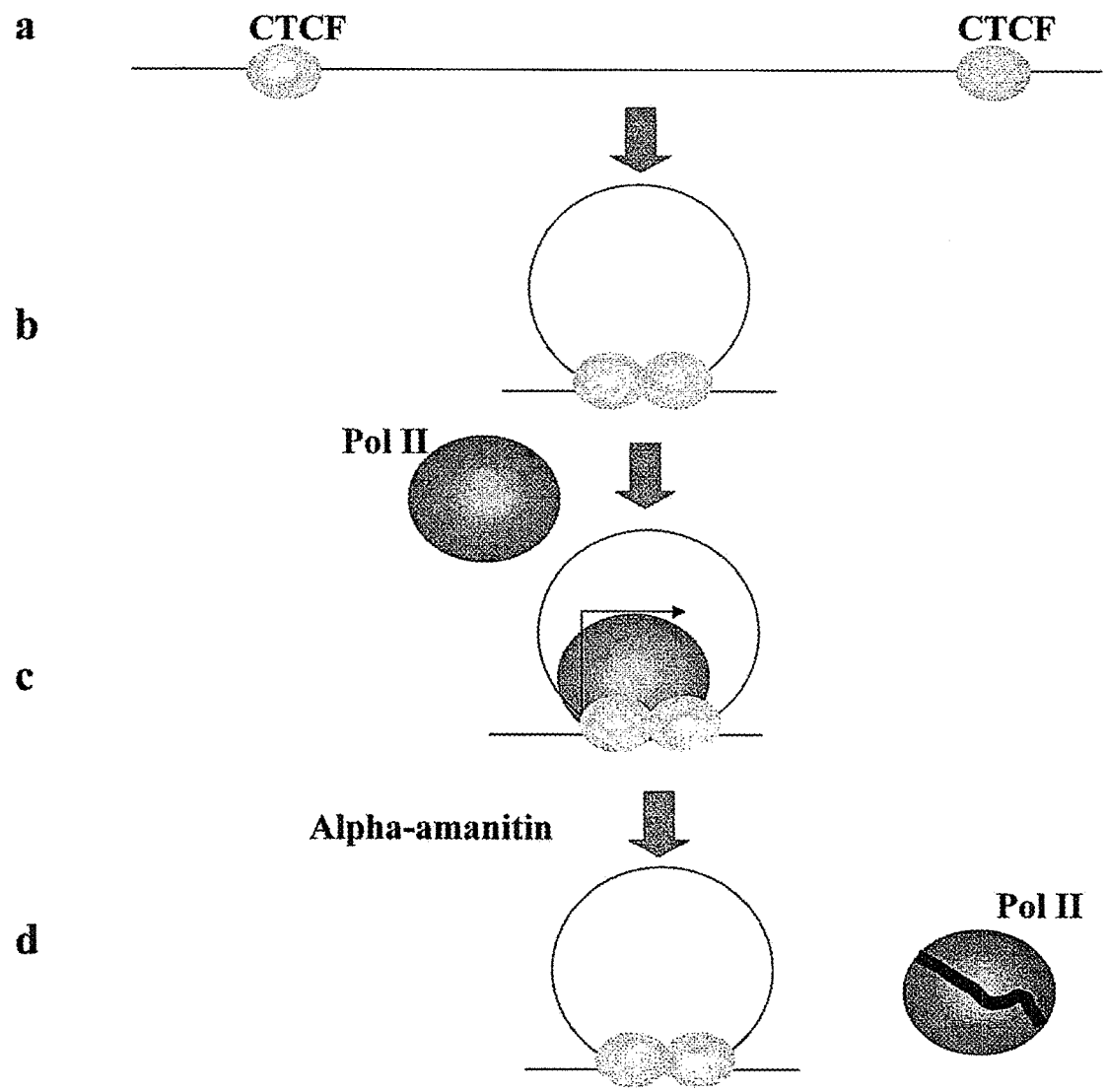

FIG. 11. A model showing how CTCF can link transcription with the high-order chromatin structures. a, CTCF binds to two sites in the 5' and 3' ends of the pN-MycLuc wt. b, The high order structure is established between the 5' and 3' ends of the pN-MycLuc wt via CTCF. c, Pol II binds to CTCF and initiates transcription; d, Following the inhibition of transcription and removal of Pol II the remaining structure can still be detected due to its association with CTCF.

EXAMPLE 1

Epigenetic Control of the GAL Locus

Conditional Antisense Transcripts at GAL10.

Addition of glucose to a culture of cells growing in galactose results in rapid inhibition of transcription. As expected, within 15 minutes of addition of glucose levels of both the 2.25 kb GAL10 transcript and the longer 4.1 kb GAL10-7 fusion transcript (Greger and Proudfoot, 1998, Embo J 17, 4771-4779; St. John and Davis, 1981, J Mol Biol 152, 285-315) drop dramatically (FIG. 1A). An antisense transcript has been reported at the repressed GAL10 gene (Perocchi et al, 2007, Nucleic Acids Res 35, e128; Samanta et al, 2006, Proc Natl Acad Sci USA 103, 4192-4197; David et al, 2006, Proc Natl Acad Sci USA 103, 5320-5325; Miura et al, 2006, PNAS 103, 17846-17851). The inventors have investigated whether antisense transcripts are a general feature of the GAL10 gene and, if so, when these transcripts appear.

In induced cultures, three antisense transcripts where observed (FIG. 1B), two of which are similar in size to the 2.25 kb and the 4.1 kb sense transcripts at the induced GAL locus (FIG. 1A). The third detectable antisense transcript is smaller, about 1.5 kb. The autoradiographs in FIGS. 1A and 1B were hybridized to probes of similar specific activity and were exposed for similar lengths of time suggesting that at the active GAL10 gene, antisense transcripts make up a significant proportion of the total RNA. Moreover, even the endogenous 4.1 kb GAL10-7 transcript, extended over both genes (FIG. 1A, C) is matched by an equivalent antisense transcript (FIG. 1B, C).

During glucose repression, the abundance of the GAL10 antisense transcripts drops considerably (FIG. 1B). As a result, two exposures of the northern blot in FIG. 1B are shown for clarity. The data in FIG. 1 demonstrates that the size of the antisense transcripts at the repressed locus also changes. Kinetic studies indicate that 15 minutes after addition of glucose to the culture, a switch is observed from the 4.1 kb, 2.25 kb and 1.5 kb antisense transcripts to three transcripts, about 3.5 kb, 2.4 kb and 1.5 kb. Both the 2.25 kb and the 2.4 kb transcript can be detected 15 minutes after glucose addition. Thus the abundance and size of the antisense transcripts at GAL10 reflects whether the gene is induced or repressed raising the interesting possibility that the antisense transcripts might play regulatory roles at the GAL locus in both conditions.

Mapping the Transcripts Around GAL10 Using RT-PCR.

Reverse transcription (RT) with strand specific primers coupled to PCR was used to determine the position of the sense and antisense transcripts around GAL10 in cells cultured in glucose, raffinose and galactose (FIG. 2). The strategy used here employed RT primers, specific for detection of either sense (S) or antisense (AS) transcripts and nested PCR primers to yield products approximately 200 bp (FIG. 2A). First the 2.25 kb GAL10 sense transcript and its equivalent antisense were analysed. These are relatively abundant transcripts amenable to mapping by RT-PCR (FIG. 2B). The GAL10 sense transcript can be detected with primer sets 6S to 8S located across the GAL10 coding region only in samples prepared from cells cultured in galactose (FIG. 2B, lane 2). A signal from primer sets 6AS to 8AS, designed to reverse transcribe and amplify antisense transcripts, is also evident only when the cells are cultured in galactose (FIG. 2B, lane 5). This suggests that the sense and antisense transcripts at induced GAL10 extend over the same regions.

In glucose and raffinose, however, were detected signals with the antisense specific primer sets 7AS and 8AS but not with 6AS or any of equivalent primers for the sense transcript. This is in agreement with the global microarray mapping which shows the transcript arising within the GAL10 coding region about 500 bp from the 3' end in repressing conditions (Perocchi et al, 2007, Nucleic Acids Res 35, e128; David et al, 2006, Proc Natl Acad Sci USA 103, 5320-5325). This suggests there are two distinct antisense transcripts over GAL10 corresponding to the induced and repressed state. If the 2.4 kb antisense transcript at the repressed locus starts within the GAL10 coding region it is likely to extend into the GAL10-1 intergenic region, confirmed with signals from primer sets 9 and 10 (FIG. 2C).

Signals for primer sets 5S and 5AS, located over the GAL10-7 intergenic region, are much weaker suggesting that the majority of the sense and antisense transcripts terminate or initiate, respectively, within this region. It was noted that sense and antisense specific primer sets for the GAL7 region also revealed evidence for sense and antisense transcripts (FIG. 2C). In this case, primer sets 3S and 3AS, spanning the end of the ORF and the 3' region, were able to detect the sense transcript but not the antisense, suggesting that the antisense transcript is promoted further upstream. The data indicate that the transcripts might be offset with respect to one another. It is concluded that GAL10 and GAL7 produce both sense and antisense transcripts when cells are induced with galactose and that the transcripts are similar in size.

Mapping the Antisense Transcripts Around GAL10 Using Northern Blots.

Northern blots with strand specific probes were used to identify the approximate position of the antisense transcripts in cells cultured in glucose, raffinose and galactose around GAL10 from three different strain backgrounds (FIG. 3). The northern blots have the advantage of being able to correlate the size of a transcript with its position at the GAL locus. Probes 2 and 3 routinely showed poor hybridization with high background signals making the hybridization to long transcripts hard to discern.

In induced culture high levels of antisense RNA to GAL7 and GAL10 are evident (probes 2 and 4) confirming the RT-PCR data in FIG. 2. The 2.25 kb antisense at induced GAL10 shows slight hybridization with probe 3 but none with probe 5 suggesting that it is confined mainly to the GAL10 ORF region. Probe 6 hybridizes to the GAL1 sense transcript as GAL1 is on the Watson strand. Two other transcripts are only produced in induced cells. These both arise within GAL1 and extend on the sense strand through the GAL1 terminator and into FUR4. One transcript is approximately >5 kb and the second is much larger.

In repressed cultures, the 2.4 kb (GAL10) antisense transcript showed strong hybridization to a short probe in the GAL10-1 intergenic region and less strongly to a GAL1 probe. No hybridization to these probes is seen with RNA prepared from cells cultured in galactose, consistent with the PCR mapping in FIG. 2. This suggests the GAL10 antisense transcript at the repressed locus arises about 500 bp from the 3' end of the GAL10 ORF and extends over the GAL10-1 intergenic region. In a similar way, the longer 3.5 kb antisense GAL10 transcript also shows strong hybridization to these probes suggesting it also extends across the GAL10-1 intergenic region and into GAL1 (FIG. 3A).

Four small non coding transcripts are evident in cells cultured in both repressing and inducing conditions (FIG. 3A). Notably, these transcripts occur predominantly over the intergenic regions at the locus. The first is a 1 kb transcript detectable at the GAL7-10 intergenic region with a probe in the antisense orientation with respect to the GAL10 and GAL7 transcripts (Probe 3). The second is a transcript of approximately 600 bp that hybridizes with a sense orientation probe to the GAL1 terminator (Probe 7). The third transcript is about 1.7 kb and extends antisense from the 5' region of KAP104 and through the GAL7 terminator region (Probe 1). The fourth is about 1.5 kb and initiates within GAL10 and extends into the GAL10-1 intergenic region (Probe 5).

In this analysis, RNA was prepared from three different strain backgrounds. The BY4741 (lane 1) and W303-1a (lane 2) strains produced similar profiles in all three carbon sources. In the YMH147 strain (lane 3), however, expression of the GAL locus appears to be derepressed in raffinose. At some regions, the transcript profile in this strain is different to that in glucose or galactose (compare for example lanes 1 and 3 in the three carbon sources at hybridized with Probes 3, 6 and 7).

A summary of the mapping data (from FIGS. 1-3) is shown in FIG. 3B. There are three notable points. The first is the relatively high level of antisense transcripts for each of the sense transcripts when cells are induced with galactose (GAL10, GAL7 and GAL10-7). Sense and antisense transcripts at the induced locus appear to be paired and synergistic. The second is the change in the size of the antisense transcripts on repression (in glucose) coupled to changes in the predicted initiation and termination sites at GAL10. Third is the presence of transcripts over the intergenic regions (GAL7 terminator; GAL10-7 intergenic region; GAL10-1 intergenic region; GAL1 terminator) at the both the repressed and induced locus.

Sequences at the 3' Region of GAL10 are Required for Induction of the Sense Transcript.

The data suggests that the position of antisense transcripts over at GAL10 reflect whether the gene is repressed or induced. These transcripts are likely to be initiated at different sites (FIG. 4A). The inventors designed an experiment to identify sequences required for induced antisense transcription (likely to arise at or near the 3' flanking sequences of GAL10) by separating the 3' flanking region from the main gene. This construct allowed testing for a putative promoter and examination of its effect on induction of the sense transcript. 554 bp between bases 2453 and 3007 were deleted leaving 92 bp at the 3' end of the GAL10 ORF and the 3' flanking sequences intact. The deleted region was also replaced by an expression cassette in the same direction as GAL10 expression. RNA was prepared from cells cultured in raffinose and transferred to galactose for 15 and 60 minutes, sufficient for strong induction of the sense transcript and the appearance of the induced 2.3 kb antisense transcript in the wild-type (FIG. 4B lane 5 and 7). The insertion at 3'end of GAL10 is sufficient to compromise expression of both the 2.4 kb and the 3.5 kb GAL10 antisense transcripts (FIG. 4B, lanes 6 and 8). Importantly, very low levels of sense transcript in these samples were observed (FIG. 4B, lanes 6 and 8). Thus, despite the promoter region for sense transcription being intact production of the sense RNA is compromised in the strain with the insertion at 3'end of GAL10. This raises the possibility that the antisense transcript is required for transcription from the GAL10 promoter. The induction profiles at GAL7 and GAL1 (FIG. 4C) were also examined in the mutant strain. No obvious effect on the repressed levels at the GAL cluster was observed. In addition, there was little effect of this insertion on induction of transcripts at GAL7 or GAL1.

Thus sequences at the 3' end of GAL10 are required for the production of the induced antisense transcript which is in turn implicated in efficient transcription of the induced sense transcript. This suggests coordination of events between the 5' and 3' ends of the induced gene.

Sequences at the 3' Region of GAL10 are not Required for Antisense Transcription at the Repressed Locus.

At the repressed locus, the antisense transcripts are likely to initiate at a different position within the GAL10 ORF (FIG. 4A). The insertion at the 3'end of GAL10 allowed us to ask whether similar sequences are required for antisense transcription at the repressed locus as at the induced locus (FIG. 4B). Surprisingly, only a small reduction in the size of the two antisense transcripts in the mutant compared to the WT was noted. The levels and the relative size difference between the long and short antisense remained very similar to those in the WT. This suggests that sequences at which these transcripts normally initiate have been deleted or disrupted by the 3' end insertion and that both transcripts are initiating at a new site, slightly closer to the 5' region of GAL10. This raises question of how these transcripts are promoted, given that their normal initiation site has been removed. One explanation is the sequences in the inserted expression cassette.

However, as these new transcripts are not present in the induced conditions, it is unlikely that they are promoted from sequences within the inserted cassette. Thus there are different sequence requirements for the induced antisense transcript and the antisense at the repressed locus.

Hda1 Recruitment to GAL10 Reflects Levels of Antisense Transcript but not H3K18Ac.

As there is significantly more antisense transcript produced when GAL10 is in the induced compared to the repressed state, experiments to ascertain if Hda1 association at GAL10 reflects either the level of antisense RNA or whether expression of the gene is induced or repressed were undertaken. Hda1-myc association with GAL10 was assessed by ChIP using chromatin prepared from induced or repressed cells (FIG. 5A). Eaf3, a component of both the Rpd3 S lysine deacetylase and the NuA4 lysine acetyltransferase (Allard et al, 1999, EMBO J 18, 5108-5119) was used as a control. Strains lacking Eaf3 show high levels of histone acetylation at the promoter and within the coding region of genes instead of the normal profile in which levels are high at the promoter and drop in the coding region, suggesting a major effect of loss of Eaf3 on the Rpd3S complex in particular (Reid et al, 2004, Mol Cell Biol 24, 757-764).

Hda1-myc is associated with both the 5' and the 3' region of GAL10 in induced cells. The signal for Hda1-myc drops about 5 fold on the repressed chromatin. This difference is not due to differences in the levels of Hda1-myc in the cells cultured in repressed or inducing conditions (data not shown). This data is consistent with the presence of high levels of antisense transcript in induced cells and high levels of Hda1 across GAL10. Eaf3 shows a similar but less pronounced trend showing lower levels of association at both the promoter and the 3' end of GAL10 on repression (FIG. 5B).

To identify if there is a relationship between Hda1 association and histone acetylation at repressed and induced GAL10 H3K18ac, a known substrate for Hda1 was examined. Levels of H3K18ac at the repressed gene are low, similar to levels in an H3K18R strain, consistent with active deacetylation by Hda1. In induced cells levels of H3K18ac are significantly higher than in repressed cells, despite high levels of Hda1 in the induced strain (FIG. 5C). This difference is present even when nucleosome loss that accompanies active transcription at GAL10 is taken into account and the H3K18ac signal is normalized to H3 levels. This suggests no direct correlation between Hda1 association and H3K18ac at GAL10. If Hda1 activity is related to antisense transcripts as proposed by Camblong et al, 2007 Cell 131, 706-717, then the high levels of H3K18ac on the induced gene, particularly at the 5' region, can be explained by the histone acetylation that accompanies transcriptional activation and elongation of the sense transcript. The balance of acetylation and deacetylation would be shifted to result in a net gain of H3K18ac on the induced gene.

Long-Range Chromatin Interactions at the GAL Locus.

Long-range chromatin interactions, also known as gene loops, have been described at a limited number of active yeast genes (Ansari and Hampsey, 2005, Genes Dev 19, 2969-2978; O'Sullivan et al, 2004, Nat Genet 36, 1014-1018; Singh and Hampsey, 2007, Mol Cell 27, 806-816). These interactions represent juxtaposition of the 5' and 3' regions of yeast genes and are associated with RNAPII, TFIIB and the CPF transcription termination machinery. Given the data showing active antisense transcription at the repressed GAL locus and 3' to 5' end communication at the induced GAL locus, investigation to ascertain if long-range interactions are implicated in antisense regulation of GAL expression was undertaken. The GAL locus was analysed for the presence of long range interactions and, by including an immunoprecipitation step, whether these interactions are associated with RNAPII and TFIIB.

Interactions between the GAL10 5' and 3' regions, the GAL7 5' and 3' region and the 5' region of GAL10 with the 3' region of GAL7 from cells cultured in glucose, raffinose and galactose were monitored using a modified 3C (chromosome conformation capture) technique (Dekker, 2006, Nat Methods 3, 17-21; Dekker et al, 2002, Science 295, 1306-1311; O'Sullivan et al, 2004, Nat Genet 36, 1014-1018) (FIG. 6A). As a control the previously detected long range interaction at FMP27, which is associated with RNAPII and is present in all three growth conditions was used (see FIG. 7C).

Long Range Interactions at the Repressed GAL Locus.

Long range interactions are detectable over GAL10, GAL7 and between the 5' region of GAL10 and the 3' region of GAL7 (GAL10-7) in cells cultured in glucose (FIG. 6B). Moreover, these interactions are associated with RNAPII as the 3C interactions can be immunoprecipitated with antibodies to Rbp1. Controls for the GAL10 and the GAL10-7 interactions show that the PCR products are specific and depend on formaldehyde crosslinking, digestion of the chromatin with DpnII, the ligation reaction and addition of template to the PCR reaction (FIG. 6C). In some reactions more than one PCR product was observed. These PCR products were isolated from gels and the sequences over the DpnII junctions were analyzed. This revealed, for example, that the DpnII site abutting primer set 6 at the GAL10-1 intergenic region is partially protected in the cross-linked chromatin preparation, resulting in a product of about 550 bp in addition to the 260 bp product expected for the long range interaction over GAL10. Similar analyses at the three long range interaction sites confirmed each of the PCR products observed is dependent on formaldehyde crosslinking and is consistent with valid long range interaction showing juxtaposition of distant sequences.

The limited number of long range interactions described to date, have been observed on actively transcribed genes. The interactions described here occur at a locus that is repressed for GAL expression although the presence of antisense transcripts suggests the locus is transcriptionally active. The next step was to examine whether the mechanism driving loop formation at repressed loci is similar to that at active genes. Long range interactions are reduced in a strain carrying the sua 7-1 allele, expressing a version of TFIIB with an E62K (glutamic acid 62 to lysine) substitution (Singh and Hampsey, 2007, Mol Cell 27, 806-816). This mutation is defective in interactions at the 3' region but not at the 5' region of active genes. In repressed conditions, the GAL10, GAL7, GAL10-7 and the control FMP27 long range interactions all showed dependence on functional TFIIB suggesting that loops on repressed loci have the same requirements as those on active genes (FIG. 6D). In addition, the GAL10 and the GAL7 long range interactions, but not that GAL10-7, can be enriched in immunoprecipitates from a strain expressing TFIIB-myc compared to an untagged strain (FIG. 6B). This suggests that TFIIB-myc is closely associated with the chromatin regions that show long range interactions at GAL10 and GAL7. The reason for the inability to detect TFIIB associated with the long range interaction across GAL10 and GAL7 is not clear, as functional TFIIB is required for the interaction. One possibility is that the epitope tag is not accessible at this interaction. Thus long range interactions can be detected at the repressed GAL locus and these interactions show the same requirements as gene loops on active genes.

A Conditional Long Range Interaction at the GAL Locus.

Long range interactions for GAL10 and GAL7 are also observed in raffinose, a repressing growth medium, and in galactose when the genes are expressed (FIG. 7B). In both cases, the interaction is associated with RNAPII. The long range interaction between the 5' region of GAL10 and the 3' region of GAL7 (GAL10-7), however, depends on the carbon source in the growth medium (FIG. 7B, C). Most importantly, this long range interaction is lost in induced conditions (galactose) and even when glucose repression is removed (in raffinose). Thus, it is unlikely that disruption of the long range interaction can be explained simply by the high levels of sense transcription which are observed under inducing conditions. Rather, the conditionality of the GAL10-7 long range interaction appears to be related to loss of glucose repression.

Long Range Interactions at the GAL Locus are Influenced by Lysine Deacetylases.

Non-coding transcripts and long range interactions are present at the GAL locus in both repressing and inducing conditions. The presence of non-coding transcripts is related to the long range interactions was investigated. The antisense transcripts are associated with the Hda1 lysine deacetylases (FIG. 5) (Camblong et al, 2007 Cell 131, 706-717). At the repressed and induced GAL10 locus, the level of chromatin associated Hda1 correlates with level of antisense transcript. It was queried if Hda1 and Eaf3 are required for the long range interactions at the GAL locus and at FMP27.

Loss of Hda1 has a dramatic effect on the long range interactions over GAL10, GAL7 and GAL10-7 in repressed cells (FIG. 6B). The effect on FMP27 is much less dramatic. By contrast, Eaf3 is required for the long range interaction at FMP27 and GAL10, but there is a lesser requirement for this factor at GAL7 or GAL10-7. Some loci, such as FMP27 and GAL7 show specificity for one or the other complex, while loci such as GAL10 appear to require both activities. This data implicate the lysine deacetylases, Hda1 and Rpd3S, directly or indirectly, in the formation a long range interactions and suggest that this may be linked to antisense transcripts.

Discussion

The inventors have used the GAL locus as a model system in which to compare the induced and repressed states and observe differences in antisense transcript and epigenetic regulation. They show that gene repression is a proactive state involving the regulated production of antisense transcripts in association with epigenetic changes to the locus.

The non-coding transcript map at the GAL locus is complex and conditional. The presence of relative short transcripts over the intergenic regions is reminiscent of promoter associated transcripts associated with yeast genes such SER3 (Martens et al, 2004, Trends Genet 23, 126-133), IMD2, LEU4 (Davis and Ares, 2006, Proc Natl Acad Sci USA 103, 3262-3267) and Ty1 (Berretta et al, 2008 Genes Dev 22, 615-626) or mammalian genes such as DHFR (Martianov et al, 2007, Nature 445, 666-670). As these are present at both the induced and repressed GAL locus they are unlikely to have regulatory functions related to activation and repression directly but may influence other aspect of locus topology.

The size and position of the non-coding antisense transcripts at GAL10 change with growth conditions. At the induced locus, there is one abundant antisense transcript whose levels rise and fall synergistically with the sense transcript. The data suggests that sequences at the 3' flanking region of GAL10 are required to promote expression of this transcript. In addition to binding sites for the Ga14 regulator (this region also contains the promoter for GAL 7) there are also Reb1 binding sites in this region. As this is a conditional transcript, a dual role for Ga14 in activating both the GAL 7 transcript and the GAL10 antisense is possible. However, the inventors have also mapped a high level antisense transcript arising at the 3' region of induced GAL 7 and there are no Ga14 binding sites in this region. Given that loss of the GAL10 antisense transcript is associated with low levels of the GAL10 sense transcript, and the demonstration of long range interactions between the 3' and 5' region of GAL10 and GAL 7, an alternative possibility is that promoter sequences play a role in activating in trans the antisense transcripts.

The antisense transcripts at induced GAL10 share properties with two genes previously shown to be associated with antisense RNA. Like PHO5 (Uhler et al, 2007, Proc Natl Acad Sci USA 104, 8011-8016), the antisense transcript at induced GAL10 is linked to transcription of the sense transcript. The GAL10 transcript is different from that at PHO5 as it does not appear to extend into the promoter region and thus is unlikely to function in the way proposed for PHO5 by remodeling promoter chromatin. Like PHO84 (Camblong et al, 2007 Cell 131, 706-717), the presence of antisense transcript correlates with the association of the Hda1 lysine deacetylase (KDAC) with chromatin. Although lysine deacetylases are associated with both activation and repression of gene expression (Bernstein et al, 2000, Proc Natl Acad Sci USA 97, 13708-13713), at PHO84 Hda1 functions with the antisense transcript to repress the sense promoter (Camblong et al, 2007 Cell 131, 706-717). Paradoxically, high levels of H3K18ac are maintained over the active GAL10 gene suggesting that acetylation associated with sense transcription shifts the dynamic balance towards acetylation. Underlying this is a ground state of active repression through KDACs and antisense transcripts. The inventors suggest that this ground state is represented in part by the long range interactions over GAL10 and GAL 7 (FIG. 7E). In this model the long range interactions, although associated with RNAPII and TFIIB, would represent a poised not active transcription as previously envisaged (Ansari and Hampsey, 2005, Genes Dev 19, 2969-2978; O'Sullivan et al, 2004, Nat Genet 36, 1014-1018; Singh and Hampsey, 2007, Mol Cell 27, 806-816). In yeast, flies and mammals many genes exist in a stable poised state with engaged RNAPII and the associated epigenetic modifications at the promoter (Guenther et al, 2007, Cell 130, 77-88; Radonjic et al, 2005, Mol Cell 18, 171-18; Zeitlinger et al, 2007, Nat Genet 39, 1512-1516).

At the induced GAL locus, antisense transcription extends over the same general region as the sense transcription. On repression there is a switch in the initiation site and a change in the nature of the sequences required to promote antisense transcription. Moreover, the antisense transcript becomes dominant. Long exposures of Northern blots, however, reveal very low levels of equivalently sized sense transcripts suggesting that the relationship between sense and antisense transcription is maintained even on a repressed gene. This reinforces the idea of "active" repression and supports the repressed state being a variation of the events that occur on activation. One natural consequence of dominant antisense transcripts is active repression through KDACs such as Hda1 and Eaf3. It is interesting that at the repressed locus the antisense transcripts extend over the GAL10$^{-1}$ intergenic region in a similar way to the exosome regulated antisense transcript at PHO84 (Camblong et al, 2007, Cell 131, 706-717769). Deacetylation over this region and other intergenic region may promote or stabilize long range interactions at the locus, for example the interaction over GAL10-7.

Also prominent on the map are long transcripts extending from one gene to another. These transcripts are conditional, for example the GAL1:FUR4 long transcript at the induced locus or the GAL10-1 antisense transcript at the repressed locus. Long non-coding transcripts are observed at the β-globin locus in mammalian cells and may be involved in conditional switches (Gribnau et al, 2000, Mol Cell 5, 377-386). In yeast, these transcripts may simply reflect poor transcript processing. Alternatively, they may be the first indication of two different types of transcription event (repressive or activating) driving or breaking higher orders of organization of yeast genes.

Experimental Procedures

Strains

Three different strain backgrounds were used in this study: BY4741 (MATa his3Δ1 leu2Δ0 met15Δ0 ura3Δ0), W303-1a (MATa, ura3-52, leu2-3-112, his3-11, ade2-1, can1-100, trp1Δ2) and YMH14 (MATa, cyc1-5000, cyc7-67, ura3-52, leu2-3-112, cyh2). The sua7-1 allele is in the YMH14 background (Pinto et al, 1994, J Biol Chem 269, 30569-30573). Strains, including epitope tagged derivatives, truncations and gene deletions were constructed by single step gene replacement using PCR-generated DNA fragments (Longtine et al, 1998, Yeast 14, 953-961). A pTEF:KanMX: TEFter was inserted into the 3' region of GAL10 resulting in loss of residues 2453 and 3007 with respect to the ATG. Transcription of the selectable marker is in the same direction as GAL10 sense transcription. SUA7 was tagged at the C terminus with the myc epitope in BY4741. hda1Δ and eaf3Δ deletions were constructed in the BY4741 background.

Media and Culture Conditions.

Growth media were prepared using standard methods in YE supplemented with 2% glucose, raffinose or galactose as required. Yeast were taken from fresh plates and grown to an OD 600 of 0.6 to 0.8 in 50 to 100 ml. Yeast were harvested by centrifugation and washed in H$_2$O before transfer to fresh medium.

Chromatin Immunoprecipitation Protocol

Chromatin immunoprecipitation was performed as described (Meluh and Broach, 1999, Nature 445, 666-670; Morillon et al, 2005, Mol Cell 18, 723-734). In summary, ChIP was done using 50 ml cultures fixed with 1% formaldehyde for 15 minutes followed by addition of glycine at 0.25 mM final. Yeast cells were broken using glass beads on a MagnaLyser (Roche) and fixed chromatin sheared by sonication using a bioruptor (Diagenode). Average DNA fragment lengths were 150 to 300 bp. After centrifugation (30 min 10K, 4° C.), the soluble chromatin was incubated with antibody to the following epitopes; 5 µl of H3 (Abcam), 5 µl of H3K18ac (Upstate), 20 µl of Eaf3 (Abcam), 10µ of Y80 (Santa Cruz) and 10 µl of myc (Sigma) in 1.5 ml siliconised Eppendorfs at 4° C. for 15 to 20 hours and immunoprecipitated with protein A sepharose for 90 minutes at room temperature. After washing, the chromatin was eluted from the beads at 65° C. for 30 minutes. Cross-links were reversed by incubation at 65° C. for 6 to 20 hours and treated with protease and RNase A. DNA was purified using Qiagen PCR mini-columns and eluted in 100 µl water. IP samples and controls e.g. no antibody, no tag, were used neat while control DNAs (input) were diluted accordingly. Samples were subject to real time PCR using a Corbett Rotorgene and Sybr Green mix (Sensymix, Quantace). Real time PCR was used to amplify regions corresponding to those shown at GAL10. Data was calculated (IP-No antibody)/TOT and expressed as a percentage of input. Error bars reflect the standard deviation of the average signal obtained between different experiments (n=2 to 4).

Generation of Strand-Specific Probes

A T7 promoter was incorporated onto the end of specific region of DNA using PCR. T7 RNA polymerase was used to generate single stranded probes with specificity for the sense or antisense strand of DNA using $^{32}$P aUTP and the Ambion MAXIscript® Kit (Cat # AM1308-AM1326).

Northern Blotting

15 µg of total RNA, prepared from cells using hot phenol:chloroform and glass beads, was separated on 1.1% formaldehyde gels and transferred to Magna nylon membranes and baked at 80° C. for 2 hours then hybridized for overnight in PerfectHyb Plus (Sigma) at 64° C., washed twice in 1×SSC/00.1% SDS, twice in 0.2×SSC. 0.1% SDS for 20 minutes each wash. Membranes were typically exposed for 24 hours unless otherwise stated. Levels of total RNA loaded was monitored by the rRNA species, which are equal across samples unless indicated.

Reverse Transcription-PCR.

For each of the ten positions across GAL10-7 in FIG. 2, there is an RT primer for the sense transcript (with respect to the direction of GAL10 expression), an RT primer for the antisense transcript, two alternative primers for the first round PCR and two alternative nested primers for the amplification. Details of the primers are given in supplementary table 1. First strand synthesis was done using the ABgene Verso cDNA kit with primers specific for the sense or antisense transcripts. A standard reaction was set up with 2 ul of RNA; primer (25 µM) 1 µl; H$_2$O 9 µl, heating to 70° C. for 5 min to remove any secondary structure and place on ice immediately. Then buffer 4 µl, dNTP 2 µl, RT 1 µl and RT enhancer 1 µl were added and the reaction incubated at 52° C. for 50 min, then for 2 min at 95° C. In RT control, reverse transcriptase was not added to the reactions. PCR amplification was a nested reaction using TakaRa DNA polymerase in the following reactions: 2× buffer I, 25 µl; dNTP (2.5 mM), 8 µl; cDNA, 2 µl; Primers (25 µM), Forward 1 µl, Reverse 1 µl; TakaRa LA Taq polymerase, 0.5 µl; H$_2$O 12. 5 µl at 94° C.-5 min, 24 cycles of 94° C.-1 min, 55° C.-45 sec, 72° C.-30 sec and 72° C.-5 min. For the second round 2 µl of the first round product was used with the nested primers in a reaction as above: 94° C.-5 min, the 18 cycles at 94° C.-45 sec, 54° C.-30 sec, 72° C.-20 sec and finally an incubation at 72° C.-5 min.

Capturing Chromosome Conformation with Immunoprecipitation (3CIP)

Nuclei were extracted from 100 ml Saccharomyces cerevisiae culture grown in appropriate medium to optical density A600=0.2. Formaldehyde was added to 1% (2.44 ml of 41%) and shaken for 10 minutes. The formaldehyde was quenched by adding glycine to 0.125M (5 ml of 2.5M). The cell pellet was washed twice in Mg/K buffer (0.1 M K2HPO4/KH2PO4 (35:65 ratio), 5 mM MgC12, pH 6.5) and resuspended in spheroplasting buffer (1.2M sorbitol, 500 U yeast lytic enzyme and 25 mM DTT in Mg/K buffer) for 15 minutes at room temperature. Spheroplasts were washed once in MES buffer (0.1M MES, 1.2M sorbitol, 1 mM EDTA, 0.5 mM MgC12 adjusted to pH 6.4 using NaOH) at 4° C. and resuspended in 10 ml MES lysis buffer (0.1M MES, 1 mM EDTA, 0.5 mM MgCl2 pH6.4). The spheroplasts were lysed using 10 strokes with a hand held homogeniser. The lysate was layered onto a sucrose gradient (5 m1 1.8M sucrose, 10 ml 1.1 M sucrose in MES lysis in a Corex tube) and separated by centrifugation for 10 min at 10,000 RPM in Beckman JA-17 rotor. The nuclei pellet was located at the interface on the glass wall. The pellet at the bottom of the tube is removed using a water wash and discarded. The nuclei pellet was washed of the glass with CSK buffer (100 mM NaC1, 300 mM sucrose, 10 mM PIPES, 3 mM MgC12, 1 mM EGTA, 0.5% Triton X-100, 10 M leupeptin, 1:1000 AEBSF) at 4° C., washed again and resuspended in 1 ml of CSK buffer and left for 20 minutes on ice. The nuclei were pelleted and all but ~100 µl of the supernatant removed. 40 µl 5M NaCl was added and incubated for 10 min on ice. The viscous mixture was diluted with 1.2 ml H$_2$O. Antibody was added and the mixture rotated at 4° C. overnight. ~40 µl of protein G-sepharose slurry (20-30 µl of beads) was prepared by washing twice in H$_2$O and once with 1 ml of restriction wash buffer (50 mM Tris-HCl (pH=8.1), 100 mM NaCl, 10 mM MgCl$_2$) and centrifugation at 2000 rpm for 3 min to collect the beads. The chromatin mixture was incubated with rotation for 60 minutes and the beads collected by centrifugation at 1000 rpm for 3 min, washed 3 times with 1 ml restriction wash buffer by rotate at 4° C. for 5 min and spinning at 2000 rpm for 3 min. 10 µl of 10× buffer 3, 50 U restriction enzyme and water to 100 µl and the chromatin digested overnight at 37° C. overnight for DpnII, or 25° C. for CviQI, then at 65° C. for 10 min to kill restriction enzyme. Heat insensitive enzymes such as CviQI were removed by washing the beads twice with restriction wash buffer. The mixture was diluted and ligated with 410 µl of H2O, 60 µl of 10× ligation buffer 30 µl (12000 U) T4 ligase and incubated at 16° C. for 4 hrs. The mixture was incubated overnight at 65° C. to de-crosslink. 1 µl of 1 mg/ml RNAase A was added and incubated at 37° C. for 30 min followed by 60 µl of 20 mg/ml Proteinase K and incubated at 42° C. for one hour. The DNA was extracted using 660 µl phenol:chloroform: isoamyl alcohol and precipitated with 30 µl of 5M NaCl, 0.5 µl 10 mg/ml glycogen and 1 ml cold ethanol and incubated at −80° C. for one hour. The pellet was collected, washed and resuspended in 20 µl H$_2$O. The following controls were included in the protocol as recommended (Dekker, 2006, Nat Methods 3, 17-21): The immunoprecipitation step was excluded to do a straight 3C procedure. For both the 3C and the 3C with IP, RNAase or Proteinase K treatments were included before the ligation step to demonstrate dependence on RNA or protein. The protocol was conducted on nuclei isolated without the formaldehyde treatment step. The immunoprecipitation steps were done after restriction and ligation step using a standard ChIP protocol (see above). The products of the reaction were detected using nested PCR using TakaRa polymerase in a 50 µl reaction. Primer stocks were 2504. The first reaction contained 25 µl of GC buffer I, 8 µl dNTP solution (1.25 mM each), 1 µl template, 1 µl of each primer, 13.5 µl H$_2$O, 0.5 µl TakaRa DNA polymerase (5 U/µl) for 25 cycles (94° C. 5 min-[94° C. 45 s, 60° C. 30 s, 72° C. 20 s]-72° C. 5 min). The second reaction contained 25 µl of GC buffer I, 8 µl dNTP solution (1.25 mM each), 2 µl template from the first reaction, 1µ of each primer, 12.5 µl H₂O, 0.5 µl TakaRa DNA polymerase (5 U/µl) for 18 cycles (94° C. 5 min-[94° C. 45 s, 61° C. 30 s, 72° C. 20 s]-72° C. 5 min). As there are four possible products for each long range interaction, all combinations of primers, except forward:forward, were included in the initial analysis. Only data with one primer combination is shown. The primer orientation (forward F; reverse R) is given relative to the direction of ORF. Each set is nested with an inner (i) and outer (o) primer (see Table 2). PCR reactions were controlled by omitting template or DNA polymerase. Templates to control for primer efficiency were prepared by ligating DpnII restricted genomic DNA. The control templates and experimental templates were titrated to determine the linear range of amplification; only one equivalent product on this range is shown for each sample.

TABLE 1

Primers for RT-PCR analysis

RT Sense Gene Specific primers

|   |   | 5'                          3' |   |
|---|---|---|---|
| 1. | S1KAP104 | CTGTAAAAGAGTTGC | (SEQ ID NO 1) |
| 2. | INF1GAL7 | CTGCAACATCCAAT | (SEQ ID NO 2) |
| 3. | INF2GAL7 | AAGGACCACTCTTAC | (SEQ ID NO 3) |
| 4. | S1GAL7 | CATGTGAAACCAAC | (SEQ ID NO 4) |
| 5. | INFIGAL10 | CTACTTTACCAAACG | (SEQ ID NO 5) |
| 6. | S1GAL10 | CAAGGTTACACAATC | (SEQ ID NO 6) |
| 7. | S2GAL10 | CTTCACCAGCAGTC | (SEQ ID NO 7) |
| 8. | S3GAL10 | GCAAGATAGCAAAC | (SEQ ID NO 8) |
| 9. | S4GAL10 | TTAGCTCTACCACAG | (SEQ ID NO 9) |
| 10. | INF1GAL1 | TGGTTATGAAGAGG | (SEQ ID NO 10) |

RT Anti Sense Gene Specific primers

| 1. | INR1GAL7 | CAAGGCTCATTGTC | (SEQ ID NO 11) |
|---|---|---|---|
| 2. | INR2GAL7 | ACGGAGTGACAATA | (SEQ ID NO 12) |
| 3. | AS2GAL7 | CTTGGTTGGTTTTG | (SEQ ID NO 13) |
| 4. | AS1GAL7 | TGGTGCTTAGAATC | (SEQ ID NO 14) |
| 5. | INR1GAL10 | CTACAGATTTTCCTG | (SEQ ID NO 15) |
| 6. | AS1GAL10 | AGGTGATCTATTGGT | (SEQ ID NO 16) |
| 7. | AS2GAL10 | GCAAGATTTGTGAC | (SEQ ID NO 17) |
| 8. | AS3GAL10 | GTTTTGGTTACAGG | (SEQ ID NO 18) |
| 9. | INR1GAL1 | GTGAAGACGAGGAC | (SEQ ID NO 19) |
| 10. | S1GAL1 | CAATCACTTCTTCTG | (SEQ ID NO 20) |

First round PCR Primers

| 1Fwd. | FKAP1041 | ATAGTCTTCGGCGGGCTTC | (SEQ ID NO 21) |
|---|---|---|---|
| 1Rev. | RKAP1041 | CGATGGAAATCCTGCACCTA | (SEQ ID NO 22) |
| 2Fwd. | FGAL71 | CGTAATAAACTTCAACAGAGCCTAAA | (SEQ ID NO 23) |
| 2Rev. | RGAL71 | TTCTAGTTATGTAAGAGTGGTC-CTTTC | (SEQ ID NO 24) |
| 3Fwd. | FGAL73 | TTGTCACTCCGTTCAAGTCG | (SEQ ID NO 25) |
| 3Rev. | RGAL73 | GCCTCAAAGAGATTTAACTTCG | (SEQ ID NO 26) |
| 4Fwd. | FGAL75 | ACCAGTCGCATTCAAAGGAG | (SEQ ID NO 27) |
| 4Rev. | RGAL75 | TGAAGTTTCGCAAGAATTGAAA | (SEQ ID NO 28) |
| 5Fwd. | FGAL101 | GCGCTTCGCAATAGTTGT | (SEQ ID NO 29) |
| 5Rev. | RGAL101 | TTGCCAGCTTACTATCCTTCTTG | (SEQ ID NO 30) |
| 6Fwd. | FGAL103 | CATCAATGTATCTACCAGGCTCA | (SEQ ID NO 31) |
| 6Rev. | RGAL103 | AAATTGACTGCTGGTGAAGC | (SEQ ID NO 32) |
| 7Fwd. | FG10AS2 | ATTTTGAATGATGGGTCCC | (SEQ ID NO 33) |
| 7Rev. | RG10AS2 | AGATTTCAAGCCACGTTTGC | (SEQ ID NO 34) |
| 8Fwd. | FGAL105 | TGGCGTATTTCGTATGACCA | (SEQ ID NO 35) |
| 8Rev. | RGAL105 | TGTTGCTGATAACCTGTCGAA | (SEQ ID NO 36) |
| 9Fwd. | FGAL107 | TGGATGGACGCAAAGAAGTT | (SEQ ID NO 37) |
| 9Rev. | RGAL107 | GCTCGGCGGCTTCTAATC | (SEQ ID NO 38) |
| 10Fwd. | FGAL11 | CGAATCAAATTAACAACCATAGGA | (SEQ ID NO 39) |
| 10Rev. | RGAL11 | AATACAAACTGAAAATGTTGAAAGT | (SEQ ID NO 40) |

Nested PCR primers

| 1Fwd. | FKAP1042 | AAAACCAAAGACTGCGGAAT | (SEQ ID NO 41) |
|---|---|---|---|
| 1Rev. | RKAP1042 | TCCGGGTTATAGAGTTTTGCTT | (SEQ ID NO 42) |
| 2Fwd. | FGAL72 | TGTCAATAAAGTGGAAATGTGTCA | (SEQ ID NO 43) |
| 2Rev. | RGAL72 | GAATTTTAGGAATACAATGCAGCTT | (SEQ ID NO 44) |
| 3Fwd. | FGAL74 | GAAACCAGGCAGTTAATAGAAAAA | (SEQ ID NO 45) |
| 3Rev. | RGAL74 | GCTGCTGAAAAACTAAGAAA | (SEQ ID NO 46) |
| 4Fwd. | FGAL76 | TTAAAATCGAGGCGAGGTC | (SEQ ID NO 47) |
| 4Rev. | RGAL76 | TGATTTGTTTGCCGATTACG | (SEQ ID NO 48) |
| 5Fwd. | FGAL1 02 | GCGGCTCGTGCTATATTCTT | (SEQ ID NO 49) |
| 5Rev. | RGAL1 02 | TTGCTGTATAACGAATTTTATGC | (SEQ ID NO 50) |
| 6Fwd. | FGAL1 04 | CCAGCAGACAAGAAATCACC | (SEQ ID NO 51) |
| 6Rev. | RGAL1 04 | TTGAGGGTACGGAGATTATGG | (SEQ ID NO 52) |
| 7Fwd. | FG10AS1 | ATTAACGCCGTTATTAACG | (SEQ ID NO 53) |

TABLE 1 -continued

Primers for RT-PCR analysis

| | | | |
|---|---|---|---|
| 7Rev. | RG10AS1 | TTCTTGGCTATGAAAATGAGG | (SEQ ID NO 54) |
| 8Fwd. | FGAL106 | GGGAATCTCGTAGCATCACC | (SEQ ID NO 55) |
| 8Rev. | RGAL106 | TGTGTGACCGAAAAGGTCTG | (SEQ ID NO 56) |
| 9Fwd. | FGAL10_8 | TGTTGTGGAAATGTAAAGAGC | (SEQ ID NO 57) |
| 9Rev. | RGAL10_8 | GCAATGAGCAGTTAAGCGTATT | (SEQ ID NO 58) |
| 10Fwd. | FGAL12 | TTTTTAGCCTTATTTCTGGGGTAA | (SEQ ID NO 59) |
| 10Rev. | RGAL12 | AAGTGGTTATGCAGCTTTTCC | (SEQ ID NO 60) |

TABLE 2

Primers for 3C analysis

| Primer designation | Sequence (5'-3') | |
|---|---|---|
| 1 GAL7 terminator R(o) | GCTCATTGTCGGTGTCGTTA | (SEQ ID NO 61) |
| 1 GAL7 terminator R(i) | CGATGGAAATCCTGCACCTA | (SEQ ID NO 22) |
| 2 GAL7 terminator F(o) | TTGTCACTCCGTTCAAGTCG | (SEQ ID NO 25) |
| 2 GAL7 terminator F(i) | TCCGAAGTTAAATCTCTTTGAGG | (SEQ ID NO 62) |
| 3 GAL10-7 intergenic R(o) | TTGCTTTGCCTCTCCTTTTG | (SEQ ID NO 63) |
| 3 GAL10-7 intergenic R(i) | CGTTTGGTAAAGTAGAGGGGGTA | (SEQ ID NO 64) |
| 4 GAL10-7 intergenic F(o) | CGCACCATAATCTCCGTACC | (SEQ ID NO 65) |
| 4 GAL10-7 intergenic F(i) | CGCTTCACCAGCAGTCAAT | (SEQ ID NO 66) |
| 5 GAL10 promoter R(o) | GGGCCTACTAATCCGTATGGT | (SEQ ID NO 67) |
| 5 GAL10 promoter R(i) | TCCCAGAAGAATGTCCCTTAG | (SEQ ID NO 68) |
| 6 GAL10 promoter F(o) | GAGGAAAAATTGGCAGTAACCT | (SEQ ID NO 69) |
| 6 GAL10 promoter F(i) | GCCCCACAAACCTTCAAAT | (SEQ ID NO 70) |
| 7 FMP27 promoter F(o) | ATCAAAGCCACGCCAAAC | (SEQ ID NO 71) |
| 7 FMP27 promoter F(i) | CCTACACGCAAAGGAACTAGAGA | (SEQ ID NO 72) |
| 8 FMP27 terminator F(o) | AGCAAACCGAACATCAAACC | (SEQ ID NO 73) |

DpnII:
Primer pairs 4 + 6, 5 + 3 and 3 + 6 will detect long range interactions across GAL10.
Primer pairs 2 + 4, 3 + 1 and 1 + 4 will detect interactions across GAL7.
Primer pairs 6 + 2 and 5 + 1 and 1 + 6 will detect interactions across GAL10-7.
For the analyses shown in FIG. 5 only the last of the primer combinations for each interaction is shown.

Table 3 shows potential chromosomal positions across the Gal locus where long range interactions may occur. For each region of the chromosome, a set of forward and reverse primers is designed. Long range interaction at the gal locus is monitored by 3C analysis between the primers designed for each region of the chromosome. For example, to monitor interaction between Gal 7 and Gal 10 regions, the primers of Row 3 (274081-87) and Row 5 (278016-19) will be used. If interactions at other regions is to be monitored, other combinations of primers will be used.

TABLE 3

| Organism | Chromosome Number | Primer start position | Primer stop position | Strand |
|---|---|---|---|---|
| Yeast | II | 273036 | 273043 | + |
| Yeast | II | 273126 | 273130 | + |
| Yeast | II | 274081 | 274087 | + |

TABLE 3-continued

| Organism | Chromosome Number | Primer start position | Primer stop position | Strand |
|---|---|---|---|---|
| Yeast | II | 274838 | 274852 | + |
| Yeast | II | 278017 | 278019 | + |
| Yeast | II | 278022 | 278022 | + |
| Yeast | II | 278025 | 278026 | + |
| Yeast | II | 279321 | 279331 | + |
| Yeast | II | 279952 | 279962 | + |
| Yeast | II | 281268 | 281284 | + |
| Yeast | II | 279941 | 279959 | − |
| Yeast | II | 279595 | 279595 | − |
| Yeast | II | 274080 | 274084 | − |
| Yeast | II | 273684 | 273694 | − |

This system is equally applicable to any other chromosomal locus where long range chromosomal interactions are thought to occur. Once the region is identified, primers can be designed to identify the presence or absence of a specified long range interaction indicating a particular physiological condition.

Example II Control of Long Range Interactions by CTCF

Several transcription factors have been shown to play a role both in the long-range DNA interactions and transcription and therefore may be good candidates to provide a link between these processes. Examples include the basic transcription factor, TFIIB which was shown to organize looping of several genes in the yeast Mol Cell, 27, 806-16, and transcription factors EKLF, GATA-1 and FOG-1 responsible for long-range DNA interactions in the β-globin gene (Drissen et al, 2004, Genes Dev, 18, 2485-90; Vakoc, et al, 2005, Mol Cell, 17, 453-62).

The inventors have identified CCCTC-binding protein (CTCF) as another candidate to perform these functions genome-wide. CTCF is implicated both in transcriptional regulation and formation of high-order conformational intra- and inter chromosomal structures (Klenova, 2002, Semin Cancer Biol, 12, 399-414; Kurukuti et al, 2006, Proc Natl Acad Sci USA, 103, 10684-9; Zhao et al, 2006, Nat Genet, 38, 1341-7; Splinter et al, 2006, Genes Dev, 20, 2349-54). It is estimated that there are >15,000 of CTCF-binding sites in the genome (Kim et al, 2007, Cell, 128, 1231-45), however it is likely that the real number of such sites >30,000 (Vetchinova et al, 2006, Anal Biochem, 354, 85-93). In transcription, CTCF can act as a classical transcription factor; a recent report demonstrates that CTCF may control transcription directly through it's interaction with RNA Polymerase II (Pol II) (Chernukhin et al, 2007, Mol Cell Biol, 27, 1631-48). CTCF-Pol II co-localization at the transcription start sites (TSS) of active genes genome-wide further strengthens this possibility (Birney et al, 2007, Nature, 447, 799-816). Finally, CTCF can form dimers which may be important for organization of DNA loops (Pant et al, 2004, Mol Cell Biol, 24, 3497-504).

Unique properties of CTCF have prompted the inventors to investigate whether it can mechanistically link the formation of high order chromosomal structures and transcription, possibly via its association with Pol II. To investigate this minimal in vivo transcription cell systems based on two genetically modified NIH3T3 cell lines have been used. These lines carry stably integrated expression vectors containing the CTCF binding site and its mutated variant deficient for CTCF binding, fused to the promoter-less Luciferase reporter gene (pN-MycLuc wt and pN-MycLuc mut, FIGS. 8a, b).

The wild type single site, but not its mutant variant, was sufficient to drive expression from the reporter Luciferase gene (FIG. 8c) (Chernukhin et al, 2007, Mol Cell Biol, 27, 1631-48). Both, CTCF and Pol II, were present at the wild type, but not the mutant CTCF binding site (FIG. 8d), thus supporting the earlier model that CTCF helps to recruit Pol II in the absence of the endogenous promoter.

In this system transcription processes may be linked with the formation of high order DNA structures, in particular between the 5' and 3' regions of the integrated DNA pN-MycLuc wt. High-order conformational structures can be monitored by the Chromosomal Conformation Capture (3C) assay, which detects close proximity of the distant sites on the chromosomal DNA in vivo. The inventors have applied the 3C analysis to the integrated pN-MycLuc wt and pN-MycLuc mut loci. Two sites at the 5' position and 3' position (FIG. 8b) were identified as juxtaposed in the 3C assay in pN-MycLuc wt, but not in pN-MycLuc mut (FIG. 9a).

On the basis of the earlier work on the CTCF interaction and co-localization with Pol II, the inventors hypothesised that CTCF and Pol II may be linked to the formation of high-order structures on the transcribed pN-MycLuc wt gene. To investigate this, work has been undertaken to identify whether both factors are present at the newly identified juxtaposed sites (FIG. 9a). Chromatin immunoprecipitation (ChIP) assay revealed that indeed both CTCF and Pol II are present at the 5'- and 3' sites, identified as juxtaposed, in pN-MycLuc wt, but not in pN-MycLuc mut (FIG. 9b, c).

The N-Myc is a known CTCF target site and the characteristic features of the sequences within N-Myc involved in CTCF binding were previously investigated (Chernukhin et al, 2007, Mol Cell Biol, 27, 1631-48; Lutz et al, 2003, Embo J, 22, 1579-87). The high frequency of occurrence of CTCF binding sites in the genomes led us to hypothesize that there may be another potential CTCF target site at the 3' end of the Luciferase gene integrated pN-MycLuc wt (FIG. 9c). As it is difficult to predict CTCF binding from the sequence, Electrophoretic mobility shift assay (EMSA) and footprinting analysis was used to investigate if CTCF can directly bind to the identified sequences. Indeed, the binding was demonstrated by EMSA with the labelled probe containing the 3' sequences and recombinant CTCF. Footprint analysis of this sequence revealed the region protected from DNase I digestion by recombinant CTCF. Thus, taken together the ChIP, EMSA and footprinting data confirm that CTCF indeed can bind to the 3' site. Therefore it is conceivable that two CTCF molecules bound to the two sites can be involved in the formation of the juxtaposition.

To further confirm the involvement of CTCF and Pol II in the establishment of high-order structures, the 4C assay (ChIP assays with either anti-Pol II or anti-CTCF antibodies followed by the 3C) were performed. The Pol II 4C and CTCF 4C analyses demonstrated the presence of Pol II and CTCF at the 5' and 3' sites during juxtaposition in pN-MycLuc wt, but not in pN-MycLuc mut (FIG. 10a, b). From these experiments it was concluded that the establishment of the juxtapositions between the 5' and the 3' regions of the wild type active construct, pN-MycLuc wt, was associated with the presence of CTCF and Pol II at the identified sites and also with the wild type status of the construct.

Further analysed dependency of the observed phenomenon on transcription was undertaken. For this purpose cells were treated with the inhibitor of transcription, alpha-amanitin. The treatment abolished the activity of pN-MycLuc wt and pN-MycLuc mut (FIG. 8c) and led to the disappearance of Pol II, but not CTCF from the N-myc site (FIG. 8e). The Pol II 4C assay performed with the anti-Pol II antibody on treated cells did not reveal the presence of Pol II at the juxtaposition between the 5' and 3' sites. However this juxtaposition was detected with the anti-CTCF antibody (FIG. 10a, b). The 3C analysis of cells treated with alpha-amanitin confirmed the existence of the structure (FIG. 9a)

The inventors also tested whether the recombinant CTCF mixed in vitro with the linearised naked plasmid DNA, pN-MycLuc wt, could be sufficient to form juxtapositions detected in vivo. Using a 4C assay (ChIP assay in combination with 3C), structures similar to the structures formed in vivo were detected in this basic system. Significantly weaker signals were observed with the pN-MycLuc mut construct used as a control thus indicating that the detected structures were dependent on two intact CTCF sites. The presence of CTCF binding in the pN-MycLuc wt, was confirmed by ChIP assay for both 5' and 3' sites.

Taken together the data suggest that transcriptional processes require the formation of high order structures, however high order structures, in the reported case dependent on CTCF, exist without the ongoing transcription. These findings support observations that long-range DNA interactions in the β-globin gene are maintained after inhibition of transcription (Palstra et al, 2008, PLoS ONE 3, e1661).

The inventors propose a model, in which the establishment of the high order structure between the 5' and 3' ends of the pN-MycLuc wt is CTCF-dependent (FIG. 11). In this model, interaction between two CTCF molecules positioned at two distant sites leads to formation of CTCF dimer and the establishment of the DNA loop (Klenova et al, 2005, Cell Cycle, 4, 96-101). Transcriptional processes can be initiated after the establishment of this configuration. Following the inhibition of transcription and removal of Pol II, the juxtaposed structure can still be detected most likely due to its association with CTCF (FIG. 11).

This example makes use of a very simple transcription system. In this system, transcription from the promoter-less Luciferase construct was driven by CTCF interacting with Pol II through the CTCF binding site, N-Myc (Chernukhin et al, 2007, Mol Cell Biol, 27, 1631-48). It was discovered that the transcription process relied on the juxtaposition between the 5' N-Myc and the 3' end of the Luciferase gene; the second CTCF binding site was identified within the juxtaposed 3' end. It is concluded that numerous transient interactions take place continuously between CTCF molecules bound to DNA in cis and trans. Stabilisation of such quasi-stable high order chromosomal associations may be a regulated process; poly ADP-ribosylation of CTCF may be involved in such regulation (Klenova et al, 2005, Cell Cycle, 4, 96-101; Yu et al, 2004, Nat Genet, 36, 1105-10). One of the outcomes of the formation of high order structures may be initiation of a transcriptional process.

Using a minimal transcription system it was identified that CTCF is involved in the establishment and maintenance of the high-order chromatin structures, which in turn are required for ongoing transcription by RNA Polymerase II.

All references cited herein are incorporated in their entirety.

The invention claimed is:

1. A method of monitoring a change in a specific conditional long range chromosomal interaction comprising making a predefined ligated DNA of known identity from a DNA sample from a subject by a chromosome conformation capture (3C) technique comprising the steps of:
   (i) in vitro crosslinking in the DNA sample specific conditional long range chromosomal interactions between distant regions of a known chromosome locus;
   (ii) isolating the cross linked DNA from said chromosomal locus;
   (iii) subjecting said cross linked DNA to restriction digestion with an enzyme that cuts at least once within the chromosomal locus;
   (iv) ligating said cross linked cleaved DNA ends to form the predefined ligated DNA;
   (v) amplifying said ligated DNA by PCR using PCR primers that specifically amplify the predefined ligated DNA;

wherein the locus comprises a gene that is regulated by metabolic signalling which leads to an alternative expression from the gene due to a change in chromosome interactions at the locus, and wherein the chromosome interactions are not associated with an inherited genetic disorder, and wherein the locus is not the B-globin locus, and wherein the long range chromosomal interactions are not interactions between genes and their regulatory elements.

* * * * *